United States Patent
Le et al.

(10) Patent No.: US 12,109,217 B2
(45) Date of Patent: Oct. 8, 2024

(54) BIOACTIVE AGENTS INCLUDED IN FUNCTIONALIZED STARCH HAVING A SINGLE HELIX V-STRUCTURE

(71) Applicant: B-ORGANIC FILMS CORP., Montreal (CA)

(72) Inventors: Tien Canh Le, Montreal (CA); Mircea-Alexandru Mateescu, Montreal (CA)

(73) Assignee: B-Organic Films Corp., Montreal (CA)

( * ) Notice: Subject to any disclaimer, the term of this patent is extended or adjusted under 35 U.S.C. 154(b) by 143 days.

(21) Appl. No.: 15/121,993

(22) PCT Filed: Feb. 25, 2015

(86) PCT No.: PCT/CA2015/000117
§ 371 (c)(1),
(2) Date: Aug. 26, 2016

(87) PCT Pub. No.: WO2015/127537
PCT Pub. Date: Sep. 3, 2015

(65) Prior Publication Data
US 2017/0072069 A1    Mar. 16, 2017

Related U.S. Application Data

(60) Provisional application No. 61/945,495, filed on Feb. 27, 2014.

(51) Int. Cl.
| | | |
|---|---|---|
| A61K 31/593 | (2006.01) | |
| A01N 33/12 | (2006.01) | |
| A23D 9/007 | (2006.01) | |
| A23L 29/219 | (2016.01) | |
| A23L 33/10 | (2016.01) | |
| A23L 33/105 | (2016.01) | |
| A23L 33/12 | (2016.01) | |
| A23L 33/155 | (2016.01) | |
| A23P 10/40 | (2016.01) | |
| A61K 8/02 | (2006.01) | |
| A61K 8/34 | (2006.01) | |
| A61K 8/35 | (2006.01) | |
| A61K 8/73 | (2006.01) | |
| A61K 9/20 | (2006.01) | |
| A61K 31/122 | (2006.01) | |
| A61K 31/202 | (2006.01) | |
| A61K 31/366 | (2006.01) | |

(Continued)

(52) U.S. Cl.
CPC ............ *A61K 31/593* (2013.01); *A01N 33/12* (2013.01); *A23D 9/007* (2013.01); *A23L 29/219* (2016.08); *A23L 33/10* (2016.08); *A23L 33/105* (2016.08); *A23L 33/12* (2016.08); *A23L 33/155* (2016.08); *A23P 10/40* (2016.08); *A61K 8/022* (2013.01); *A61K 8/347* (2013.01); *A61K 8/35* (2013.01); *A61K 8/732* (2013.01); *A61K 9/2059* (2013.01); *A61K 31/122* (2013.01); *A61K 31/202* (2013.01); *A61K 31/366* (2013.01); *A61K 47/6949* (2017.08); *A61Q 5/02* (2013.01); *A61Q 5/12* (2013.01); *C08B 31/04* (2013.01); *C08B 31/12* (2013.01); *C08J 3/12* (2013.01); *C08K 5/0041* (2013.01); *C08K 5/01* (2013.01); *C08K 5/05* (2013.01); *C08K 5/07* (2013.01); *C08K 5/103* (2013.01); *C08K 5/14* (2013.01); *A61K 2800/56* (2013.01); *C08J 2300/14* (2013.01); *C08J 2303/04* (2013.01); *Y02A 50/30* (2018.01)

(58) Field of Classification Search
CPC ............ A61K 47/48961; A61K 31/366; A61K 31/202; A61K 31/593; A61K 31/122; C08K 5/103; C08K 5/05; C08K 5/07; C08K 5/0041; C08K 5/01; C08K 5/14; C08K 5/03; C08L 3/08; C08L 3/06; A01N 33/12; A01N 25/10; A01N 25/12
See application file for complete search history.

(56) References Cited

U.S. PATENT DOCUMENTS 4,451,649 A * 5/1984 Teubner ................. C08B 31/12
106/206.1
4,985,082 A * 1/1991 Whistler ................. A61Q 19/00
127/32

(Continued)

FOREIGN PATENT DOCUMENTS

CA    2591806    6/2006
JP    2005530866 A   10/2005

(Continued)

OTHER PUBLICATIONS

Beenackers et al. "Novel Processes or the Carboxymethylation of Starch," 1998, 4(17) Supl., pp. 1-14. (Year: 1998).*

(Continued)

*Primary Examiner* — Doan T Phan
(74) *Attorney, Agent, or Firm* — Kilpatrick Townsend & Stockton LLP

(57) ABSTRACT

The present document describes a powder composition comprising a functionalized starch having a single helix V-structure and having a degree of substitution of at least 0.25, and a bioactive agent, forming an inclusion complex with said functionalized starch, where the bioactive agent is within the helix V-structure of the functionalized starch having a single helix V-structure. Also described are the functionalized starch having a single helix V-structure and having a degree of substitution of at least 0.25, methods of making the same and methods of using the same to manufacture the powder composition.

14 Claims, 18 Drawing Sheets

(51) Int. Cl.
*A61K 47/69* (2017.01)
*A61Q 5/02* (2006.01)
*A61Q 5/12* (2006.01)
*C08B 31/04* (2006.01)
*C08B 31/12* (2006.01)
*C08J 3/12* (2006.01)
*C08K 5/00* (2006.01)
*C08K 5/01* (2006.01)
*C08K 5/05* (2006.01)
*C08K 5/07* (2006.01)
*C08K 5/103* (2006.01)
*C08K 5/14* (2006.01)

(56) References Cited

U.S. PATENT DOCUMENTS

| | | | |
|---|---|---|---|
| 5,879,707 | A | 3/1999 | Cartilier et al. |
| 2006/0035009 | A1* | 2/2006 | Gaonkar ............... A61K 31/575 426/658 |
| 2008/0206325 | A1* | 8/2008 | Bouquerand ........ A61K 9/1652 424/463 |
| 2010/0008982 | A1* | 1/2010 | Shimoni ............. A61K 9/1652 424/451 |
| 2012/0178597 | A1 | 7/2012 | Januszek |
| 2012/0189567 | A1* | 7/2012 | Gupta ..................... A61K 8/49 424/62 |

FOREIGN PATENT DOCUMENTS

| | | |
|---|---|---|
| WO | 8904842 A1 | 6/1989 |
| WO | WO9943305 A1 | 9/1999 |
| WO | 2004075921 A1 | 9/2004 |
| WO | 2007026307 A2 | 3/2007 |
| WO | 2007026883 A1 | 3/2007 |
| WO | 2007122624 A2 | 11/2007 |
| WO | 2013163738 A1 | 11/2013 |

OTHER PUBLICATIONS

Spychaj et al. (2013). "Medium and High substituted carboxymethyl starch: synthesis, characterization and application." Starch, (65): 22-33. (Year: 2013).*

International Search Report of PCT/CA2015/000117; May 13, 2015; Owen Terreau.

Luo, Z.-G. et al., "Preparation of Acetylated Waxy, Normal, and High-Amylose Maize Starches with Intermediate Degrees of Substitution in Aqueous Solution and Their Properties", Journal of agricultural and Food Chemistry, vol. 60, No. 37, pp. 9468-9475, Published Sep. 4, 2012.

Supplementary European Search Report of 15754841.3; Munich; Nov. 15, 2017; Zellner, Armin.

English Translation of Corresponding Japanese Patent Application No. 2016-571450 mailed on Nov. 13, 2018.

* cited by examiner

Floating phenomena of a commercial soft-gel capsule and of Omega-3 oil released from soft-gel capsule at 37°C in simulated gastric fluid (pH 1.5).

Molecular Structure

Molecular Geometries
adapted from
Immel and Lichtenthaler, 2000.
*Starch/Stärke*, 52, 1-8

Native Starch

Double Helix

Carboxymethyl Starch

Single Helix

Native Starch

Commercial Carboxymethyl Starch
(according to Rowe *et al.* 2009.
Handbook of Pharmaceutical Excipients,
Pharmaceutical Press)

Carboxymethyl Starch in the
present invention
(obtained by carboxymethylation of
starch partially hydrolyzed with
amyloglucosidase)

BIOACTIVE AGENTS INCLUDED IN FUNCTIONALIZED STARCH HAVING A SINGLE HELIX V-STRUCTURE

CROSS-REFERENCE TO RELATED APPLICATIONS

This application is a US National Phase application under 35 USC § 371 of PCT/CA2015/000117, filed Feb. 25, 2015, which claims priority from and the benefit of U.S. Provisional Application No. 61/945,495, filed on Feb. 27 2014, the specifications of which are hereby incorporated by reference in their entireties.

BACKGROUND

(a) FIELD

The subject matter here disclosed generally relates to compositions of functionalized starch and bioactive agents, as well as to methods of making the same. More specifically, the subject matter disclosed generally relates to compositions of functionalized starch having a single helix V-structure, and at least a bioactive agent, complexed to the functionalized starch having a single helix V-structure, and methods of making the same.

(b) Related Prior Art

In the present invention, Bioactive Agents (BA) are defined as poorly water-soluble or water insoluble compounds, or as particularly liposoluble compounds which can provide health benefits for human or animal. BA can be natural products such as plant (e.g. essential oils) or animal (fish oils) extracts, vitamins, drugs and other chemical or biological molecules including pesticides (herbicides, insecticides, bactericides, fungicides and sanitizers). For other liposoluble compounds such as saturated fatty acids (e.g. palmitic acid) or even unsaturated but with trans-configurations, they are not considered as part of BA, because they do not provide beneficial or therapeutic effects for human or animals.

Important BA are polyunsaturated fatty acids such as Omega-3 which cannot be synthesized by the human body. These Bioactive Agents are beneficial, especially in cardio-vascular diseases and in several immune system disorders.

For instance, Omega-3 such as eicosapentaenoic acid and docosahexaenoic acid are mainly provided by dietary intake, but often in insufficient quantities and thus, in certain conditions (recovery, post-surgery, adsorption dysfunction, elders, etc.) supplements are frequently recommended. The interest for Omega-3 as dietary supplement is continuously growing due to their essential role in human health.

The Omega-3 naturally occur mainly as triglycerides (TG) but are commercially marketed under fatty acid ethyl ester (FAEE) of free fatty acids that are semi-synthetic forms. Production of FAEE involves trans-esterification of Omega-3 with ethanol. The digestion of FAEE generates free fatty acids and ethanol, which can cause some side effects on children or people with deficient alcohol dehydrogenase. Furthermore, the fatty acid ethyl ester is approximately 50 times more resistant to pancreatic lipase as compared to lipolysis of natural Omega-3 under TG forms.

Generally, commercial Omega-3 liquid encapsulated in soft-gel capsules with enteric coating remains stable in gastric fluid. However, this dosage form presents inconveniences such as eructation with fishy aftertaste, probably due to a longer residency of the capsule in the stomach. Furthermore, the capsule is often floating in the gastric fluid during the transit period and the Omega-3 can be released mainly in stomach and remain on the surface of gastric fluid (FIG. 1) reducing thus their availability for intestinal adsorption.

Food enrichment with Omega-3 constitutes another alternative. Unfortunately, Omega-3 are generally difficult to disperse in food products due to their hydrophobicity and bad taste. In addition, Omega-3 are unstable and susceptible to oxidation in the presence of light and oxygen often resulting the formation of a variety of toxic degradation products. Some of these degradation products are aldehydes (i.e. malondialdehyde) that, in addition to toxicity, have an unpleasant smell and taste, leading to off-flavors or even change of color in such food products fortified with Omega-3.

For these reasons, it is of interest to encapsulate Omega-3 under microcapsules that are small particles containing bioactive agents inside a shell. Numerous biocompatible polymers (i.e. beeswax, gelatin and polyacrylic acid) are often used as coating or shell material which play a role as barrier to protect against oxidation, light and thereby masking off-flavors.

Generally, methods of microencapsulation of Omega-3 are based on the spray-drying of emulsion (atomization of BA solution in fine droplets at high temperature to obtain the powders) or coacervation complexes. However, these methods tend to have high oils levels at surface. In order to overcome this obstacle, another approach «multicore microcapsules» have been developed (WO 2006/085227 A2). In fact, these multicore microcapsules comprise an agglomeration of primary microcapsules and each individual primary microcapsule has a primary shell. The resulting encapsulated agglomeration is thereafter coated by an outer shell, may be prepared by providing an aqueous mixture of a loading substance and a shell material (U.S. Pat. No. 6,974, 592 B2).

However, the manufacture of «multicore microcapsules» involves numerous steps. The use of chemical reagents (i.e sodium polyphosphate to trigger the agglomeration in acidic medium) and enzyme (trans-glutaminase as cross-linker for hardening of microcapsules) followed by spray-drying at high temperature to obtain powder forms are limiting factors.

Also, similar approaches are disclosed in WO 2003/015528 for the encapsulation of long chain polyunsaturated fatty acids using «multi-component starch-based matrix» comprising starch hydrolysate, maltodextrin and cyclodextrin, and even lecithin as emulsifying agent.

Generally, these methods (multicore or multicomponent) are complicated, and involve multi-steps and for certain procedures require special equipment to manufacture. The use of chemical reagents and/or enzyme and the addition of preservatives (i.e. ascorbic acid to prevent oxidation of Omega-3 during the production) contribute significantly to the elevated price of final products, limiting thus their affordability and applications. In addition, the recovery yield is variable and is difficult to estimate the concentration of BA with precision.

SUMMARY

According to an embodiment, there is provided a powder composition comprising:
   a functionalized starch having a single helix V-structure and having a degree of substitution of at least 0.25, and a bioactive agent, forming an inclusion complex with the functionalized starch, wherein the bioactive agent is within the helix V-structure of the functionalized starch having a single helix V-structure.

The degree of substitution may be from about 0.25 to about 1.5, or from about 0.4 to about 0.7.

The functionalized starch having a single helix V-structure may be a carboxylated starch, a hydroxypropylated starch, an acetylated starch, a hydroxypropyl methylated starch, an aminated starch, an alkylated starch, an acylated starch, an acid modified starch, an octenylated starch, a pregelatinized starch, or combinations thereof.

The carboxylated starch may be carboxymethyl starch, carboxyethyl starch, succinyl starch, octenyl succinyl starch, acryloyl starch, acetyl starch or combinations thereof.

The carboxylated starch may be carboxymethyl starch.

The functionalized starch having a single helix V-structure may be prepared from a native or a non-native starch, or a combination thereof.

The native starch may be a corn starch, a potato starch, a pea starch, a rice starch, a bean starch, a wheat starch, or combinations thereof.

The non-native starch may be a carboxymethyl starch, a hydroxypropyl starch, an acetyl starch, a hydroxypropyl methyl starch, an amine starch, an alkyl starch, an acyl starch, an acid modified starch, an octenyl succinyl starch, a pregelatinized starch, a cross-linked starch.

The carboxylated non-native starch may be a carboxymethyl starch, a carboxyethyl carboxymethyl starch, a carboxymethyl hydroxypropyl starch, a carboxymethyl hydroxypropyl methyl starch, a carboxymethyl acetyl starch, a carboxymethyl octenyl succinyl starch, a carboxymethyl acryloyl starch, a carboxymethyl acyl starch, a carboxymethyl alkyl starch, a carboxymethyl cross-linked starch, or combinations thereof.

The functionalized starch having a single helix V-structure may be prepared from a partially hydrolyzed starch.

The non-native starch may be a partially hydrolyzed non-native starch.

The partially hydrolyzed starch may be physically partially hydrolyzed starch, chemically partially hydrolyzed starch, or enzymatically partially hydrolyzed starch.

The physically partially hydrolyzed starch may be obtained by gamma irradiation.

The chemically partially hydrolyzed starch may be obtained by an acid treatment.

The acid treatment may be a hydrochloric acid treatment, a phosphoric acid treatment, a sulfuric acid treatment or combinations thereof.

The enzymatically partially hydrolyzed starch may be obtained by an alpha-amylase treatment, a beta-amylase treatment, an amyloglucosidase treatment, an isoamylase treatment, or combinations thereof.

The bioactive agent may be a simple fatty acid, a lipid-like compound, a complex lipid, an antibiotic, a protein, a peptide, or combinations thereof.

The bioactive agent may be a pharmaceutically active ingredient.

The simple fatty acid may be alpha-linolenic acid, eicosapentaenoic acid, docosahexaenoic acid, or combinations thereof.

The complex lipid may be a glyceride, a carotenoid, a terpenoid, an isoprenoid, a withanolide, a cholesterol, a phytosterol, a liposoluble vitamin, a stilbenoid, and combinations thereof.

The glyceride may be omega-3 monoglyceride, omega-3 diglyceride, omega-3 triglycerides, or combinations thereof.

The carotenoid may be beta-carotene, retinoic acid and its derivatives, lutein, zeaxanthin, lycopene, and astaxanthin, or combinations thereof.

The terpenoid may be a mono-terpene, a sesqui-terpene, a di-terpene, a sester-terpenes, a tri-terpenes, derivatives thereof, and combinations thereof.

The derivates of terpenes may be a boswellic acid, a pentacyclictriterpene, artemisinin, and coenzyme Q10, or combinations thereof.

The stilbenoid may be resveratrol.

The complex lipid may be a mixture of at least one of astaxanthin, beta-carotene, zeaxanthin, lycopene and resveratrol, with omega-3.

The withanolide may be withaferin or derivative of withanolide such as salpichrolides, nicandrenones, and ixocarpalactone.

The phytosterol may be campesterol, stigmasterol, or combinations thereof.

The liposoluble vitamin may be vitamin $D_2$ (ergocalciferol) and its derivatives, vitamin A (trans-retinol) and its derivatives, vitamin $D_3$ (cholecalciferol) and its derivatives, vitamin E (tocopherol) and its derivatives, vitamin K (phytomenadione), or combinations thereof.

The ratio of the functionalized starch having a single helix V-structure and the bioactive agent may be from about 12:1 to 1:2, respectively.

The powder composition may be soluble in an aqueous media.

The powder composition may be dispersible in an aqueous media.

According to another embodiment, there is provided a food comprising the powder composition of the present invention, and a food ingredient.

The food may be a juice, a dairy product, and a soft drink.

According to another embodiment, there is provided a cosmetic comprising the powder composition the present invention, and a cosmetically acceptable carrier.

The cosmetic may be a cream, a lotion, a facial masks, a shampoo, a conditioner, a paste, a spray, a gel, or a mousses.

The bioactive agent may be astaxanthin, resveratrol, polyphenol, Coenzyme Q10, or combinations thereof.

According to another embodiment, there is provided a pharmaceutical composition comprising the powder composition of the present invention, and a pharmaceutically acceptable carrier.

The bioactive agent may be artemisinin and its derivatives; paclitaxel, docetaxel and combinations thereof; clopidogrel and/or warfarin;

According to another embodiment, there is provided a disinfectant comprising the powder composition of the present invention, wherein the bioactive agent may be a quaternary ammonium compound, and a suitable carrier.

According to another embodiment, there is provided a method of treating malaria comprising administering to a subject in need thereof at least one of a powder composition of the present invention, wherein the bioactive agent may be artemisinin, and the pharmaceutical composition of the present invention.

According to another embodiment, there is provided a method of treating a cancer comprising administering to a subject in need thereof at least one of a powder composition of the present invention, wherein the bioactive agent may be paclitaxel, docetaxel and combinations thereof, and the pharmaceutical composition of the present invention.

According to another embodiment, there is provided a method of inhibiting or preventing blood clotting comprising administering to a subject in need thereof at least one of a powder composition of the present invention, wherein the bioactive agent may be clopidogrel, and the pharmaceutical composition of the present invention.

According to another embodiment, there is provided a use of a powder composition of the present invention, wherein the bioactive agent may be artemisinin, or the pharmaceutical composition of the present invention for the treatment of malaria.

According to another embodiment, there is provided a use of a powder composition of the present invention, wherein the bioactive agent may be paclitaxel, or the pharmaceutical composition of the present invention for the treatment of cancer.

According to another embodiment, there is provided a use of a powder composition of the present invention, wherein the bioactive agent may be clopidogrel, or the pharmaceutical composition of the present invention for inhibiting or preventing blood clotting.

According to another embodiment, there is provided a method of disinfecting a non-living surface comprising contacting the surface with the disinfectant according to the present invention.

According to another embodiment, there is provided a use of a powder composition of the present invention, for the fabrication of a medicament.

According to another embodiment, there is provided a process for the preparation of a water-soluble or dispersible powder composition comprising contacting a functionalized starch having a single helix V-structure and having a degree of substitution of at least 0.25 in powder form with a bioactive agent; and aerating the functionalized starch having a single helix V-structure and having a degree of substitution of at least 0.25 in powder form and the bioactive agent for a time sufficient to obtain an inclusion complex of the functionalized starch having a single helix V-structure and having a degree of substitution of at least 0.25 powder and the bioactive agent.

The degree of substitution may be from about 0.25 to about 1.5 or from about 0.4 to about 1.0.

The functionalized starch having a single helix V-structure may be a carboxylated starch, a hydroxypropylated starch, an acetylated starch, a hydroxypropyl methylated starch, an aminated starch, an alkylated starch, an acylated starch, an acid modified starch, an octenylated starch, a pregelatinized starch, or combinations thereof.

The carboxylated starch may be carboxymethyl starch, carboxyethyl starch, succinyl starch, octenyl succinyl starch, acrylated starch and combinations thereof.

The carboxylated starch may be carboxymethyl starch.

The functionalized starch having a single helix V-structure may be prepared from a native or a non-native starch, or a combination thereof.

The native starch may be a corn starch, a potato starch, a pea starch, a rice starch, a bean starch, a wheat starch, or combinations thereof.

The non-native starch may be a carboxylated starch, a hydroxypropylated starch, an acetylated starch, a hydroxypropylated methyl starch, an aminated starch, an alkylated starch, an acylated starch, an acid modified starch, an octenylated starch, a pregelatinized starch, a cross-linked starch.

The carboxylated starch may be carboxymethylated starch, a carboxymethyl hydroxypropylated starch, carboxymethyl acetylated starch, a carboxymethyl cross-linked starch, or combinations thereof.

The functionalized starch having a single helix V-structure may be prepared from a partially hydrolyzed starch.

The partially hydrolyzed starch may be physically partially hydrolyzed starch, chemically partially hydrolyzed starch, or enzymatically partially hydrolyzed starch.

The physically partially hydrolyzed starch may be obtained by gamma irradiation.

The chemically partially hydrolyzed starch may be obtained by an acid treatment.

The acid treatment may be a sulfuric acid treatment, a hydrochloric acid treatment, or phosphoric acid treatment or combination thereof.

The enzymatically partially hydrolyzed starch may be obtained by an alpha-amylase treatment, a beta amylase treatment, an amyloglucosidase treatment, an isoamylase treatment, or combinations thereof.

The bioactive agent may be a simple fatty acid, a complex lipid, or combinations thereof.

The bioactive agent may be a pharmaceutically active ingredient.

The simple fatty acid may be alpha-linolenic acid, eicosapentaenoic acid, docosahexaenoic acid, or combinations thereof.

The complex lipid may be a glyceride, a carotenoid, a terpenoid, an isoprenoid, a withanolide, a cholesterol, a phytosterol, a liposoluble vitamin, a stilbenoid, and combinations thereof.

The glyceride may be Omega-3 monoglyceride, diglyceride, triglycerides, or combinations thereof.

The carotenoid may be beta-carotene, retinoic acid, lutein, zeaxanthin, lycopene, and astaxanthin, or combinations thereof.

The terpenoid may be a mono-terpene, a sesqui-terpene, a di-terpene, a sester-terpenes, a tri-terpenes, derivatives thereof, and combinations thereof.

The derivates of terpenes may be a boswellic acid, a pentacyclictriterpene, artemisinin, and coenzyme Q10, or combinations thereof.

The stilbenoid may be resveratrol.

The complex lipid may be a mixture of at least one of astaxanthin, beta-carotene, zeaxanthin, lycopene and resveratrol, with Omega-3 triglycerides.

The withanolide may be withaferin or derivative of withanolide such as salpichrolides, nicandrenones, and ixocarpalactone.

The phytosterol may be campesterol, stigmasterol, or combinations thereof.

The liposoluble vitamin may be vitamin $D_2$ (ergocalciferol) and its derivatives, vitamin A (trans-retinol) and its derivatives, vitamin $D_3$ (cholecalciferol) and its derivatives, vitamin E (tocopherol) and its derivative, vitamin K (phytomenadione), or combinations thereof.

The ratio of the functionalized starch having a single helix V-structure and the bioactive agent may be from about 12:1 to 1:2, respectively.

According to another embodiment, there is provided a process for the preparation of a functionalized starch having a single helix V-structure comprising the step of 1) reacting a starch with a functionalization reagent, in an alkaline solvent-water medium and at a temperature inferior to 30° C. for a time sufficient to functionalize the starch.

The starch may be a native or a non-native starch.

The functionalization reagent may be a carboxylic acid reagent.

The carboxylic acid reagent may be sodium monochloroacetate, sodium acrylate, succinic anhydride, octenyl succinic anhydride, or combination thereof.

The functionalization reagent may be a non-carboxylic acid reagent.

The non-carboxylic acid reagent may be ethylene oxide, propylene oxide, 3-chloro-1-propanol, 3-bromo-1-propanol, 1-chloro-2-propanol, acetic anhydride, methyl chloroacetate, 2-chloro-ethylamine hydrochloride, 3-chloropropylamine hydrochloride, (3-chloro-2-hydroxypropyl) trimethylammonium chloride, palmitoyl chloride, and combination thereof.

The solvent-water medium comprises a solvent chosen from methanol, ethanol, isopropanol, propanol, isobutanol, 1-octanol, 1-decanol, 1-dodecanol, cetyl alcohol, acetone, and combinations thereof.

The solvent-water medium may be a hydroalcoholic medium.

The hydroalcoholic medium may be an ethanol/water mixture or an isopropanol/water mixture.

The solvent-water medium comprises a ratio of solvent:water from 7:3 to 19:1.

The process may be performed at sub-optimal conditions.

The process may be performed at about 22° C.

The native starch may be a corn starch, a potato starch, a pea starch, a rice starch, a bean starch, a wheat starch, or combinations thereof.

The non-native starch may be a a carboxymethyl starch, a hydroxypropyl starch, an acetyl starch, a hydroxypropyl methyl starch, an amine starch, an alkyl starch, an acyl starch, an acid modified starch, an octenyl succinyl starch, a pregelatinized starch, a partially hydrolyzed starch and a cross-linked starch.

The partially hydrolyzed starch may be physically partially hydrolyzed starch, chemically partially hydrolyzed starch, or enzymatically partially hydrolyzed starch.

The partially hydrolyzed starch may be enzymatically partially hydrolyzed starch.

The physically partially hydrolyzed starch may be obtained by gamma irradiation.

The chemically partially hydrolyzed starch may be obtained by an acid treatment.

The acid treatment may be obtained by a hydrochloric acid treatment, a phosphoric acid treatment, a sulfuric acid treatment or combinations thereof.

The enzymatically partially hydrolyzed starch may be obtained by an alpha-amylase treatment, a beta-amylase treatment, an amyloglucosidase treatment, an isoamylase treatment, or combinations thereof.

The process may further comprise step 2): separating the functionalized starch having a single helix V-structure from the solvent-water medium.

The separating may be by filtration, decantation, or combinations thereof.

The process may further comprise step 3): washing the functionalized starch having a single helix V-structure.

According to another embodiment, there is provided a functionalized starch having a single helix V-structure and having a degree of substitution of at least 0.25.

The degree of substitution may be from about 0.25 to about 1.5 or from about 0.4 to about 0.7.

The functionalized starch having a single helix V-structure may be a carboxylated starch, a hydroxypropylated starch, an acetylated starch, a hydroxypropyl methylated starch, an aminated starch, an alkylated starch, an acylated starch, an acid modified starch, an octenylated starch, a pregelatinized starch, or combinations thereof.

The carboxylated starch may be carboxymethyl starch, carboxyethyl starch, succinyl starch, octenyl succinyl starch, acryloyl starch, acetyl starch or combinations thereof.

The carboxylated starch may be carboxymethyl starch.

The functionalized starch having a single helix V-structure may be prepared from a native or a non-native starch, or a combination thereof.

The native starch may be a corn starch, a potato starch, a pea starch, a rice starch, a bean starch, a wheat starch, or combinations thereof.

The non-native starch may be a carboxymethyl starch, a hydroxypropyl starch, an acetyl starch, a hydroxypropyl methyl starch, an amine starch, an alkyl starch, an acyl starch, an acid modified starch, an octenyl succinyl starch, a pregelatinized starch, a cross-linked starch.

The carboxylated non-native starch may be a carboxymethyl starch, a carboxyethyl carboxymethyl starch, a carboxymethyl hydroxypropyl starch, a carboxymethyl hydroxypropyl methyl starch, a carboxymethyl acetyl starch, a carboxymethyl octenyl succinyl starch, a carboxymethyl acryloyl starch, a carboxymethyl acyl starch, a carboxymethyl alkyl starch, a carboxymethyl cross-linked starch, or combinations thereof.

The functionalized starch having a single helix V-structure may be prepared from a partially hydrolyzed starch.

The non-native starch may be a partially hydrolyzed non-native starch.

The partially hydrolyzed starch may be physically partially hydrolyzed starch, chemically partially hydrolyzed starch, or enzymatically partially hydrolyzed starch.

The physically partially hydrolyzed starch may be obtained by gamma irradiation.

The chemically partially hydrolyzed starch may be obtained by an acid treatment.

The acid treatment may be a hydrochloric acid treatment, a phosphoric acid treatment, a sulfuric acid treatment or combinations thereof.

The partially hydrolyzed starch may be enzymatically partially hydrolyzed starch.

The enzymatically partially hydrolyzed starch may be obtained by an alpha-amylase treatment, a beta-amylase treatment, an amyloglucosidase treatment, an isoamylase treatment, or combinations thereof.

According to another embodiment, there is provided a functionalized starch having in an X-Ray diffraction a first band at 2-theta=12-15° and a second band at 2-theta=23-24°.

The following terms are defined below.

As used herein, the terms «functionalizing starch» or «functionalized starch» is intended to mean functionalization that are not limited to the conversion of the native or modified starch by carboxymethylation, but also include possible functionalization of other starch derivatives such as starch succinate (succinyl starch), hydroxypropyl starch, acetyl starch, hydroxypropyl methyl starch, acid modified starch, octenyl starch, pregelatinized starch or mixture thereof.

The term «functionalization» as used herein is intended to mean the addition by covalent bonds of functional groups onto the starch (or its derivatives) chains in order to promote its conversion mainly in single helix V-structure. The functionalization can be (but is not limited to) the carboxylation (addition of carboxylate groups), amination (addition of amine groups), alkylation (addition of alkyl groups) or acylation (addition of acyl groups).

The term «carboxylation» as used herein is intended to mean the addition of carboxyl groups onto the starch macromolecule. Possible carboxylation includes but not limited to the carboxymethylation, carboxyethylation, succinylation, acrylation, etc. According to a preferred embodiment, the carboxylation is a «carboxymethylation».

The term «degree of substitution» is intended to mean the average number of substituents per glucose unit (GU), the monomer unit of starch. Since each GU contains three hydroxyl groups, the DS can vary between 0-3. According to an embodiment of the present invention, the DS may be equal to or greater than 0.25 such as to obtain for certain BA up to 80% (w/w) incorporated in the functionalized starch (e.g. CMS).

The term «bioactive agent» or «active agent» or «active ingredient» is intended to mean compounds or mixtures thereof having or producing an effect on living organisms. Examples include particularly lipids (i.e. omega-3) and lipid-like molecules (i.e. cholesterol or phytosterol), hydrophobic molecules (i.e. Artemisinin and its derivatives (artesunate, artemether, arteether, dihydroartemisinin and artelinate), pharmaceutical ingredients (i.e. Clopidogrel), proteins or peptides (i.e. bacteriocin), antibiotics (i.e. cyclosporine), etc.

The term «composition» as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive, the full scope of the subject matter being set forth in the claims.

BRIEF DESCRIPTION OF THE DRAWINGS

Further features and advantages of the present disclosure will become apparent from the following detailed description, taken in combination with the appended drawings, in which.

Figure 1:
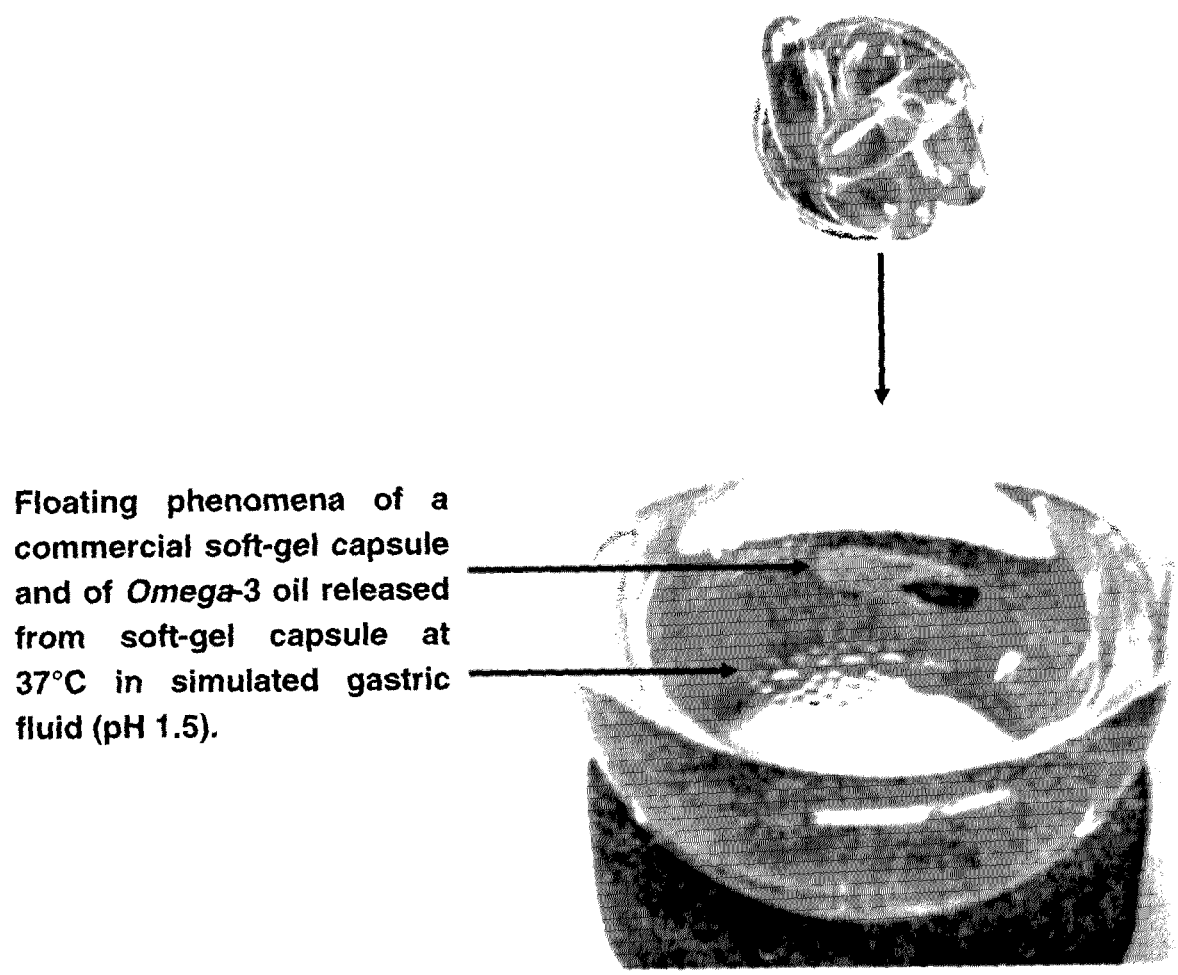
FIG. 1 illustrates the floating phenomena of a commercial soft-gel capsule and of Omega-3 oil released from the soft-gel capsule at 37° C. in simulated gastric fluid (pH 1.5).

Starch is a natural carbohydrate constituted by two major components: Amylose (non-branched) and Amylopectine (branched chains). The ratio Amylose/Amylopectine depends on the starch vegetal origin. The non-branched chains can be organized in double, or simple helices or alternated with disordered regions).

DETAILED DESCRIPTION

In a first embodiment, there is disclosed an inclusion complex powder composition comprising:
  a functionalized starch having a single helix V-structure and having a degree of substitution of at least 0.25, and
  a bioactive agent, forming an inclusion complex with the functionalized starch, wherein the bioactive agent is within the helix V-structure of the functionalized starch having a single helix V-structure.

The functionalized starch having a single helix V-structure may be a carboxymethyl starch (CMS).

According to an embodiment, to obtain an inclusion complex with a higher quantity of BA, the degree of functionalization (or degree of substitution, DS) of the functionalized starch must be sufficiently elevated in order to acquire a prominence of helix V-structure.

According to an embodiment of the present invention, the DS may be equal to or greater than 0.25 such as to obtain for certain BA up to 80% (w/w) incorporated in the functionalized starch (e.g. CMS). According to an embodiment, the DS may be from about 0.25 to about 3, or from about 0.25 to about 2.5, or from about 0.25 to about 2, or from about 0.25 to about 1.5, or from about 0.25 to about 1.0, or from about 0.25 to about 0.95, or from about 0.25 to about 0.90, or from about 0.25 to about 0.85, or from about 0.25 to about 0.80, or from about 0.25 to about 0.75, or from about 0.25 to about 0.70, or from about 0.25 to about 0.65, or from about 0.25 to about 0.60, or from about 0.25 to about 0.55, or from about 0.25 to about 0.50, or from about 0.25 to about 0.45, or from about 0.25 to about 0.40, or from about 0.25 to about 0.35, or from about 0.25 to about 0.30, or about 0.3 to about 3, or from about 0.3 to about 2.5, or from about 0.3 to about 2, or from about 0.3 to about 1.5, or from about 0.3 to about 1.0, or from about 0.3 to about 0.95, or from about 0.3 to about 0.90, or from about 0.3 to about 0.85, or from about 0.3 to about 0.80, or from about 0.3 to about 0.75, or from about 0.3 to about 0.70, or from about 0.3 to about 0.65, or from about 0.3 to about 0.60, or from about 0.3 to about 0.55, or from about 0.3 to about 0.50, or from about 0.3 to about 0.45, or from about 0.3 to about 0.40, or from about 0.3 to about 0.35, or about 0.35 to about 3, or from about 0.35 to about 2.5, or from about 0.35 to about 2, or from about 0.35 to about 1.5, or from about 0.35 to about 1.0, or from about 0.35 to about 0.95, or from about 0.35 to about 0.90, or from about 0.35 to about 0.85, or from about 0.35 to about 0.80, or from about 0.35 to about 0.75, or from about 0.35 to about 0.70, or from about 0.35 to about 0.65, or from about 0.35 to about 0.60, or from about 0.35 to about 0.55, or from about 0.35 to about 0.50, or from about 0.35 to about 0.45, or from about 0.35 to about 0.40, or about 0.4 to about 3, or from about 0.4 to about 2.5, or from about 0.4 to about 2, or from about 0.4 to about 1.5, or from about 0.4 to about 1.0, or from about 0.4 to about 0.95, or from about 0.4 to about 0.90, or from about 0.4 to about 0.85, or from about 0.4 to about 0.80, or from about 0.4 to about 0.75, or from about 0.4 to about 0.70, or from about 0.4 to about 0.65, or from about 0.4 to about 0.60, or from about 0.4 to about 0.55, or from about 0.4 to about 0.50, or from about 0.4 to about 0.45, about 0.45 to about 3, or from about 0.45 to about 2.5, or from about 0.45 to about 2, or from about 0.45 to about 1.5, or from about 0.45 to about 1.0, or from about 0.45 to about 0.95, or from about 0.45 to about 0.90, or from about 0.45 to about 0.85, or from about 0.45 to about 0.80, or from about 0.45 to about 0.75, or from about 0.45 to about 0.70, or from about 0.45 to about 0.65, or from about 0.45 to about 0.60, or from about 0.45 to about 0.55, or from about 0.45 to about 0.50, or about 0.5 to about 3, or from about 0.5 to about 2.5, or from about 0.5 to about 2, or from about 0.5 to about 1.5, or from about 0.5 to about 1.0, or from about 0.5 to about 0.95, or from about 0.5 to about 0.90, or from about 0.5 to about 0.85, or from about 0.5 to about 0.80, or from about 0.5 to about 0.75, or from about 0.5 to about 0.70, or from about 0.5 to about 0.65, or from about 0.5 to about 0.60, or from about 0.5 to about 0.55, or about 0.55 to about 3, or from about 0.55 to about 2.5, or from about 0.55 to about 2, or from about 0.55 to about 1.5, or from about 0.55 to about 1.0, or from about 0.55 to about 0.95, or from about 0.55 to about 0.90, or from about 0.55 to about 0.85, or from about 0.55 to about 0.80, or from about 0.55 to about 0.75, or from about 0.55 to about 0.70, or from about 0.55 to about 0.65, or from about 0.55 to about 0.60, or about 0.6 to about 3, or from about 0.6 to about 2.5, or from about 0.6 to about 2, or from about 0.6 to about 1.5, or from about 0.6 to about 1.0, or from about 0.6 to about 0.95, or from about 0.6 to about 0.90, or from about 0.6 to about 0.85, or from about 0.6 to about 0.80, or from about 0.6 to about 0.75, or from about 0.6 to about 0.70, or from about 0.6 to about 0.65, or about 0.65 to about 3, or from about 0.65 to about 2.5, or from about 0.65 to about 2, or from about 0.65 to about 1.5, or from about 0.65 to about 1.0, or from about 0.65 to about 0.95, or from about 0.65 to about 0.90, or from about 0.65 to about 0.85, or from about 0.65 to about 0.80, or from about 0.65 to about 0.75, or from about 0.65 to about 0.70, or about 0.7 to about 3, or from about 0.7 to about 2.5, or from about 0.7 to about 2, or from about 0.7 to about 1.5, or from about 0.7 to about 1.0, or from about 0.7 to about 0.95, or from about 0.7 to about 0.90, or from about 0.7 to about 0.85, or from about 0.7 to about 0.80, or from about 0.7 to about 0.75, or about 0.75 to about 3, or from about 0.75 to about 2.5, or from about 0.75 to about 2, or from about 0.75 to about 1.5, or from about 0.75 to about 1.0, or from about 0.75 to about 0.95, or from about 0.75 to about 0.90, or from about 0.75 to about 0.85, or from about 0.75 to about 0.80, or about 0.8 to about 3, or from about 0.8 to about 2.5, or from about 0.8 to about 2, or from about 0.8 to about 1.5, or from about 0.8 to about 1.0, or from about 0.8 to about 0.95, or from about 0.8 to about 0.90, or from about 0.8 to about 0.85, or about 0.85 to about 3, or from about 0.85 to about 2.5, or from about 0.85 to about 2, or from about 0.85 to about 1.5, or from about 0.85 to about 1.0, or from about 0.85 to about 0.95, or from about 0.85 to about 0.90, or about 0.9 to about 3, or from about 0.9 to about 2.5, or from about 0.9 to about 2, or from about 0.9 to about 1.5, or from about 0.9 to about 1.0, or from about 0.9 to about 0.95, or about 0.95 to about 3, or from about 0.95 to about 2.5, or from about 0.95 to about 2, or from about 0.95 to about 1.5, or from about 0.95 to about 1.0, or about 1.0 to about 3, or from about 1.0 to about 2.5, or from about 1.0 to about 2, or from about 1.0 to about 1.5, or about 1.5 to about 3, or from about 1.5 to about 2.5, or from about 1.5 to about 2, or about 2.0 to about 3, or from about 2.0 to about 2.5, or about 2.5 to about 3.

To obtain products with high DS, the synthesis of the functionalized starch (e.g. CMS) in the present invention is carried out in a solvent-water media and the carboxymethylation is preferably accomplished in alcohol/water medium, particularly in ethanol/water or in isopropanol/water. According to embodiment, the solvent-water medium may be a medium having a ratio of solvent:water from about 7:3 to about 19:1. In in other words from about 70% to about 95% (vol/vol) solvent in water, or from about 70% to about 90% (vol/vol), or from about 70% to about 85% (vol/vol), or from about 70% to about 80% (vol/vol), or from about 70% to about 75% (vol/vol), or from about 75% to about 95% (vol/vol), or from about 75% to about 90% (vol/vol), or from about 75% to about 85% (vol/vol), or from about 75% to about 80% (vol/vol), or from about 80% to about 95% (vol/vol), or from about 80% to about 90% (vol/vol), or from about 80% to about 85% (vol/vol), from about 85% to about 95% (vol/vol), or from about 85% to about 90% (vol/vol), or from about 90% to about 95% (vol/vol) solvent in water. It is believed that since the alkyl (i.e. isopropyl) chain of alcohol can lodge in the starch hydrophobic cavity during the functionalizing reaction, the converting from double helices in single helix is more effective and can enhance the cavity diameter.

According to an embodiment, an important difference with other methods described previously is that the functionalization of starch in the present invention may be performed under sub-optimal conditions (i.e. temperature at 28° C. or lower, instead of ≥40° C.). It is believed that these sub-optimal conditions slow down the reactivity of the reagent employed and facilitate penetration of the reagent into starch granules to obtain more uniformly functionalized starches having more pores.

Incorporation (or Inclusion) of Bioactive Agent Inside Single Helix V-Structure of Functionalized Starch The complexation between the functionalized starch (e.g. CMS) and BA in the present invention essentially occurs by BA inclusion inside the CMS helical structure which does not affect the solubility or dispersibility of the inclusion complexes in aqueous media. In contrast, the BA remained outside the helical structure reduces greatly the solubility of the complex which can even become insoluble. Therefore, according to an embodiment of the present invention, the powder composition of the present invention may be soluble in an aqueous media. According to some embodiment, depending on the BA being incorporated in the functionalized starch of the present invention, as well as its relative concentration, the functionalized starch:BA complex will be soluble in an aqueous media, providing an essentially clear solution. According to another embodiment, the powder composition of the present invention may be dispersible in an aqueous media. According to some embodiment, depending on the BA being incorporated in the functionalized starch of the present invention, as well as its relative concentration, the functionalized starch:BA complex will be dispersible in an aqueous media, providing an cloudy solution. According to some embodiments, dependent on the BA being incorporated into a complex with the functionalized starch of the present invention, at some lower concentration the complex will be soluble in an aqueous medium, while at higher concentration, the complex will be dispersible in an aqueous medium.

The phenomenon of BA occurring outside the CMS helical structure is often observed when the treatment of CMS with BA is conducted in aqueous media, even in the presence of emulsifying agent. This is probably due to: i) ionic interactions between CMS (negative charges from carboxylate groups) and certain BA possessing positive charges; and ii) hydrophobic associations between BA/BA which take place outside CMS helix structure. Generally, these undesirable interactions prevent not only the incorporation of BA inside the helical structure, but also reduce considerably the solubility or dispersibility of the CMS/BA complex.

Water is considered a kind of universal solvent due to its ability to dissolve or dissociate many compounds. In this case, water can dissociate certain BA in salt forms (i.e. Stearalkonium chloride, a quaternary compound) which are susceptible to interact with CMS. Furthermore, water is a poor solvent for liposoluble molecules which tend to promote hydrophobic associations. To limit these undesirable interactions, it is suitable to conduct the incorporation of BA inside CMS in non-aqueous media.

Several moderately polar non-aqueous solvents (i.e. methanol, ethanol and acetone) can limit ionic interactions and are able to homogenously disperse a mostly of BA, promoting thus the insertion of BA inside CMS helical structure. For these reasons, the incorporation of BA in CMS in the present invention is preferably accomplished in non-aqueous media in order to avoid the formation of BA outside of the helical structure.

For certain BA such as Omega-3 (which is generally under liquid form), the use of a solvent is not necessary. In contrast, for the BA and particularly for drugs under solid powder forms, the use of solvent seems essential. Indeed, these solid powder forms need to be dissolved in an appropriate solvent (or a mixture of solvents) under homogenous solution just prior to incorporate in the single helix V-structure of functionalized starch.

In a second embodiment, there is provided a process for the preparation of a water-soluble or dispersible powder composition comprising:

- contacting a functionalized starch having a single helix V-structure and having a degree of substitution of at least 0.25 powder with a bioactive agent; and
- aerating the functionalized starch having a single helix V-structure and having a degree of substitution of at least 0.25 powder and the bioactive agent for a time sufficient to obtain an inclusion complex of the functionalized starch having a single helix V-structure and having a degree of substitution of at least 0.25 powder and the bioactive agent.

Monoacyl lipids (such as free fatty acids, mono-glycerides, and linear alcohols) can form complexes with non-derivatized or hydrolyzed starch. It is generally believed that the complex formation is due the monoacyl lipid molecules entering within the central cavities of native starch helices. A correlation between these monoacyl lipids and the functional properties of starches was reported (Tester, R. F. and Morrison, W. R. 1990. *Cereal Chem.,* 67, 551-557). In fact, monoacyl lipids will induce the formation, during gelatinization, of amylose/lipid complexes which restrict swelling, dispersion of the starch granules and solubilization of amylose, thus generating opaque pastes with reduced viscosity and increased pasting temperatures.

To avoid these limitations, we have proposed that functionalized starch could generate mainly single helix V-structure able to complex bioactive agents while retaining its properties such as swelling, solubilization and viscosity in aqueous media.

Functionalized Starch Containing Mainly Single Helix V-Structure

Figure 2:
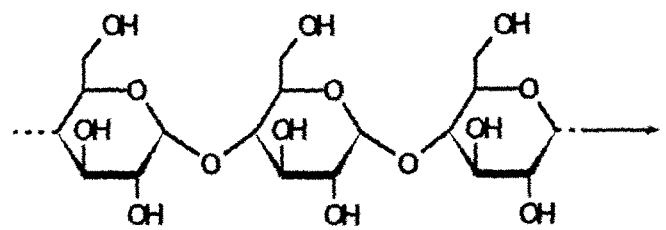
FIG. 2 illustrates a schematic presentation of native and carboxymethyl starch molecular structure and their corresponding organization for double and single helical forms.
Figure 2:
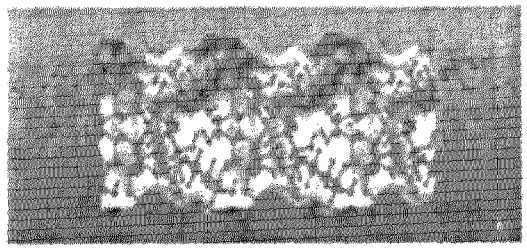
Figure 2:
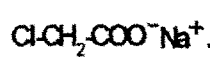
Figure 2:
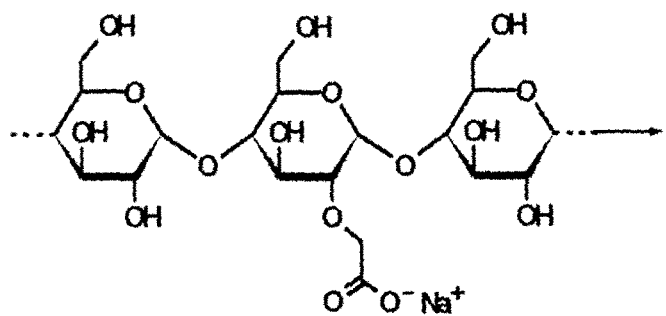
Figure 2:
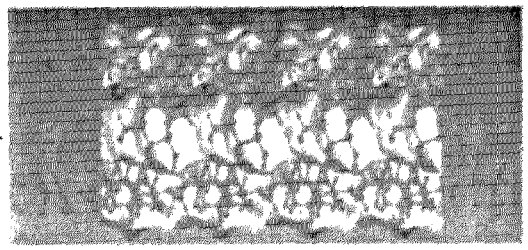

By functionalization such as carboxymethylation, starch can change its structure from a predominant double helix to a single helix structure. Moreover, the single helix V-structure generally presents a larger cavity and hydrophobic disposal more pronounced than double helix structure in the native starch (FIG. 2). Based on this difference, the present invention proposes using a functionalized starch such as carboxymethyl starch as a matrix to incorporate lipids inside its single helix V-structure. It is worth mentioning that the functionalized starch needs to be prepared under sub-optimal conditions as described in the present invention in order to obtain a higher conversion from double helices to single helix V-structure and granules more porous.

According to an embodiment, the BA incorporated in functionalized starch according to the present invention is not only single chain lipids (i.e. free fatty acid), but also lipids having more complex structures (i.e. triglycerides, carotenoids, cholesterols, phytosterols, etc.) or other poorly water-soluble compounds (i.e. antibiotics or for certain proteins or peptides).

Functionalization of Starch or its Derivatives for Incorporation of Bioactive Agents Under Mild Conditions According to an embodiment of the present invention, a new method is disclosed to obtain BA under water-soluble or dispersible powder forms using functionalized starch. According to another embodiment, the functionalized starch is a functionalized starch having mainly a single helix V-structure. Preferably, the functionalized starch may be carboxymethyl starch (CMS) or starch glycolate (SG) which are organized mainly as single helix V-structure.

According to an embodiment, not only native starch can be used as starting material for carboxymethylation, but also its derivatives such as succinyl starch, hydroxypropyl starch, acetyl starch or cross-linked functionalized starch, or mixtures thereof. It is believed that these derivatives do not generally affect the structure of the starch, particularly helix V-structure when used the method described in the present invention. For instance, it is also possible to synthesize carboxymethyl hydroxypropyl-starch, carboxymethyl acetyl-starch and/or carboxymethyl cross-linked starch in hydroalcoholic media that will permit to obtain predominantly single helix V-structure.

The incorporation of BA, i.e. Omega-3 liquid fish oil, is very simple and carried out under gentle conditions, by introducing at room temperature BA oil liquid directly into functionalized starch powders. This direct incorporation of lipids by simple spreading of liquid oil onto the solid CMS powder is similar to spray fluid bed granulation processes.

According to an embodiment, the CMS/BA powder mixture is gently stirred and airing in the dark for between about 2 h to 12 h or more, and preferably 24 h or more, in order to favor the self-rearrangement and inclusion of the BA (favorable stabilization of BA inside the helix V-structure of the functionalized starch). After stabilization, the BA powders are ready to use.

Important Aspects of BA Water Dispersible Powder Solid Forms

In embodiments, the BA included in functionalized starch having a single helix V-structure (e.g. CMS) powders of the present invention, obtained with a process of the present invention are characterized by:

- simplicity to manufacture;
- stability in drastic conditions;
- capacity to protect effectively the BA;
- compatibility with various products, particularly for the food, nutraceutic cosmetic and drug fields;
- versatility, not only under powder forms, but also under tablet form or fluidized suspensions;
- possibility to rapidly generate stable aqueous solution for various applications.

In order to highlight differences, novelties and advantages of the present invention, the comparison with other methods currently commercialized or described in previous art seems necessary and of interest.

Generally in previous art, the method commonly uses to obtain BA under solid forms is the microencapsulation. For example, Omega-3 are used as BA for microencapsulation in U.S. Pat. Nos. 6,974,592 and 7,727,629 which involves several steps:

i) dissolving the matrix (i.e. gelatin) in an aqueous medium;
ii) dispersing Omega-3 with emulsifying agent and antioxidant (i.e. sodium ascorbate) in matrix suspension;
iii) homogenizing before adding sodium polyphosphate;
iv) agglomerating to obtain microcapsules by adjusting the pH value at 4.7;
v) stabilizing microcapsules using chemical (i.e. glutaraldehyde, U.S. Pat. No. 7,727,629 B2) or enzymatic (i.e. trans-glutaminase, U.S. Pat. No. 6,974,592 B2) cross-linkers for 9 h;
vi) spray-drying to obtain the corresponding powders.

In contrast, the method of the present invention is simply carried out in two steps only:

i) adding Omega-3 liquid oil directly in carboxymethyl starch powders and mixing;
ii) aerating at least 2 h in the dark for stabilization.

A unique aspect in the present invention is that the incorporation is obtained under gentle conditions. Consequently, there are no alterations of BA structure, or of its biological activity. In addition, the BA/functionalized starch inclusion complex is mechanically resistant in biological fluids (i.e. gastric acidity) and stable at high temperatures. This inclusion complex form is able to protect effectively the BA against oxidation and light, thus enhancing its shelf-life.

According to another embodiment, the BA powders of the present invention have long term stability not only under dry state, but also after dissolving in aqueous solutions. This is important for storage and for various applications, especially in case of enrichment of aqueous products such as milk, dairy products, juices and soft drinks.

According to another embodiment, the BA that may be used in the present invention are not only limited to simple fatty acids (i.e. Alpha-Linolenic acid, Eicosapentaenoic and Docosahexaenoic acids), but also include several other complex lipids, lipid-like molecules or other poorly soluble compounds, as follows:

- glycerides (i.e. Omega-3 Triglycerides);
- carotenoids (i.e. Beta-Carotene) and its derivatives (Retinoic acid);
- terpenoids or isoprenoids including mono-terpenes, sesqui-terpenes, di-terpenes, sester-terpenes and tri-terpenes (i.e. essential oils) and their derivatives (i.e. Boswellic acid, a pentacyclictriterpene; Artemisinin, a sesquiterpene lactone containing an endoperoxide; Coenzyme Q10, an isoprenoid derivative);

withanolides (i.e. Withaferin) and its derivatives (i.e. Salpichrolides, Nicandrenones, Ixocarpalactone)

cholesterols and phytosterols and their derivatives (i.e. Campesterol, Stigmasterol, Ergocalciferol, Cholecalciferol);

liposoluble vitamins (i.e. vitamin A and derivatives retinyl acetate and retinyl palmitate, vitamin D and derivative cholecalciferol palmitate, vitamin E and derivatives tocopheryl palmitate and tocopheryl acetate, and vitamin K);

antibiotics (i.e. cyclosporins)

proteins or peptides (i.e. bacteriocins)

mixtures thereof.

Furthermore, the method of the present invention presents several advantages:

no modification required for BA (i.e. conversion of Triglyceride in fatty acid ethyl ester in the case of Omega-3)

no use of an aqueous solution for dispersion, emulsion, precipitation and consequently, no requirement of the processing to isolate the BA complex from the aqueous solution;

no use of emulsifying agents (i.e. lecithin);

no need of chemical reagents (i.e. polyphosphate as cross-linker) nor enzyme (i.e. trans-glutaminase as hardener);

no requirement of special organic solvents;

no heat treatment.

Additionally, the incorporated BA in the present invention present interesting characteristics:

soluble in aqueous media and easy to incorporate in various foods;

safe and responding to GRAS (Generally Recognized As Safe) criteria;

good protection against oxidation and light;

stable in gastric acidity;

compressible under tablet dosage forms from which BA can be formulated to immediate release or to deliver in the controlled manner to the intestinal tract (main absorption windows of liposoluble molecules);

high bioavailability.

BA Water-Soluble or Dispersible Powder Forms for Food or Nutraceutical Applications According to an embodiment, the incorporation of liquid Omega-3 fish oil in functionalized starch under powder forms allows easily to enrich aqueous based products such as milk, dairy products, juices and soft drinks or under tablet forms for dietary supplements.

BA Water-Soluble or Dispersible Powder Forms for Cosmetic Applications

According to another embodiment, BA such as Astaxanthin, Resveratrol, CoQ10, etc. under powder solid forms can be incorporated:

in creams, lotions or facial masks (anti-age, anti-wrinkles, dark-spot, etc.) for skincare;

in shampoo, or conditioners for hair care;

in pastes, sprays, gels or mousses for hair styling.

BA Water-Soluble or Dispersible Powder Forms for Pharmaceutical Applications

Antimalaria: According to another embodiment, of the present invention, the BA incorporated in solid powders are also useful for pharmaceutical applications. For instance, Artemisinin is the active principle of extracts from Chinese medicinal plant *Artemisia annua* (Quinghaosu) currently used for treatment of malaria which is a major health problem in many tropical countries.

Structurally characterized as a sesqui-terpene lactone with a peroxide bridge, Artemisinin is poorly soluble in water and oil and presents a low oral bioavailability (about 30%). For these reasons, the majority of antimalarial drugs currently on the market are mainly derivatized from Artemisinin in order to improve its solubility (i.e. Artesunate). These derivatives present a slight improvement of their solubility. However, the cost of artemisinin derivatives contributes significantly to the high price of these therapies which remain largely unaffordable to the most vulnerable populations.

Development of water-soluble or dispersible artemisinin can markedly enhance its bioavailability, reduce side effects and costs permitting to increase the access to these antimalarial drugs making them affordable to the people who mostly need them. Furthermore, water dispersible artemisinin can be easily combined with other antimalaria agents for Artemisinin-based combination therapies (as promoted by the World Health Organization, e.g. Artemether/Lumefantrine), particularly for pediatric dosage forms (suppository, syrup or instant powders for solution, etc.) and possibly to enable intravenous and intramuscular administrations.

The method of the present invention is particularly suitable to obtain such a product, because no derivatization or modification of bioactive molecules or chemical reagents is used. In this context, the incorporation of Artemisinin in the helix V-structure of carboxymethyl starch is simple to manufacture, at low cost, for generating a water-soluble or dispersible Artemisinin following the present invention.

Anticancer: According to another embodiment, other terpenoids could be used as BA, such as Paclitaxel. This agent is resulted from the investigation of over 12000 natural plant compounds for anticancer activity (Appendino, G. 1993. *Fitoterapia*. 45, 5-27).

Paclitaxel is a diterpenoid pseudoalkaloid possessing antitumor activity, which is widely used in the treatment of ovarian carcinoma and breast cancer. The intravenous administration, currently used, is inconvenient to many patients and associated with several unpredictable side effects, mainly due to the pharmaceutical vehicle, Cremophor EL (polyethoxylated castor oil).

According to an embodiment, oral administration of Paclitaxel is of interest for patient compliance and it may circumvent systemic exposure to the vehicle Cremophor EL. Furthermore, oral administration may enable development of chronic treatment schedules, which would result in sustained plasma concentrations above a pharmacologically relevant threshold level.

Paclitaxel molecule is highly lipophilic, a weak electrolyte, non-polar and consequently, poorly soluble in aqueous medium making it difficult to formulate for oral administration. Generally, there are two main problems with Paclitaxel: low solubility and scarce availability. The solubility of Paclitaxel can be improved by using various systems such as emulsions, micelles, liposomes, microspheres nanoparticles, etc. However, these systems are not stable in gastric acidity (causing release of active principles before reaching the absorption site) or at long term storage. In addition, certain vehicles are toxic, expensive and complicated to manufacture.

In contrast, the use of composition according to the present invention is of interest, making water-soluble or dispersible Paclitaxel which is stable in gastric fluid, low cost, simple to manufacture and easily to formulate under tablet dosage forms for sustained released or targeted-colon delivery.

Platelet Aggregation Inhibitor: Clopidogrel Bisulfate is an antiplatelet agent used to inhibit blood clotting in coronary artery disease, peripheral vascular disease and cerebrovascular disease. The drug works by irreversibly inhibiting the P2Y12 receptor, an adenosine diphosphate chemoreceptor on platelet cell membranes.

The most frequent adverse drug reactions with Clopidogrel Bisulfate (with or without associated Acetyl Salicylic Acid, ASA) are hemorrhage and bleeding disorders including purpura, rash, dyspepsia, abdominal pain and diarrhea. It is believed that these adverse effects are mainly caused by the formation of sulfuric acid derived from Clopidogrel Bisulfate salt forms (and by an additional acidity from Acetylsalicylic acid in the case of combination). Normally, there is no sulfate in the Clopidogrel chemical molecule; however Clopidogrel is manufactured under bisulfate salt form. Clopidogrel bisulfate is insoluble in water at neutral pH but freely soluble at pH 1-2 (similar to gastric pH), which promotes the release of Clopidogrel mainly in the stomach.

According to an embodiment of the present invention, Clopidogrel may be incorporated into CMS under powder forms, and be converted in a water-soluble or dispersible form without bisulfate salt. Furthermore, CMS is stable in gastric acidity and prevents the release of active principle in the stomach, but is soluble in intestinal fluid releasing thus water dispersible Clopidogrel in a controlled manner. In this case, the composition of the present invention can improve the availability of Clopidogrel enhance effectiveness and reduce side effects.

BA Water Dispersible Powder Forms for Agricultural Applications

According to another embodiment of the present invention, BA can also be pesticides or biocides, antibacterial or antiviral agents, particularly quaternary ammonium compounds (QAC) which possess generally a limited solubility when contain aliphatic alkyl chains. QAC are widely used as disinfectants in water and wastewater effluent treatments or as algaecides for swimming pools.

Due to their long hydrophobic hydrocarbon chains, QAC are slightly soluble and slowly dispersible and often float on the surface of water which limits thus their expandability and activity. Additionally, QAC are unstable in the environmental conditions due to their interactions mainly with organic and inorganic contaminants.

According to an embodiment of the present invention, the incorporation of QAC inside CMS helix V-structure enhances their solubility and dispersibility, not only on the surface of, but fully in water medium. Furthermore, QAC stable in the CMS V-helix cavity may be slowly released in the environment, thus prolonging its activity for a longer period of time. According to another embodiment, for certain biocides such as Benzalkonium Chloride, complexation with CMS can reduce their ecotoxicological effects on sensitive aquatic non-target organisms.

The present invention will be more readily understood by referring to the following examples which are given to illustrate the invention rather than to limit its scope.

These examples further illustrate the method of production of carboxymethyl starch used as matrix in order to incorporate bioactive agents as well as the formulations of the invention.

Example 1

Synthesis of Carboxymethyl Starch (CMS)

In the present invention, different sources of starch can be used as starting materials such as corn starch, potato starch, pea starch, rice starch, bean starch, wheat starch, etc. or combination thereof. Depending on the source of starch, the degree of substitution (DS) and the mechanical properties of obtained functionalized starch having a single helix V-structure can vary as function of different ratios of amylose and amylopectin.

For instance, the carboxymethylation from potato starch permits to obtain a derivative more soluble in water whereas that from corn starch presents a swelling gel, more stable, at the same DS.

1.1. Carboxymethylation of Potato Starch in Hydroalcoholic Media

The CMS is synthesized by etherification of native potato starch (Sigma-Aldrich, Saint Louis, MO, USA) with sodium monochloroacetate under alkaline conditions for the conversion from native starch double helix structure in single helix V-structure.

Differently to prior arts, the reaction in the present invention is carried out in alcohol/water (hydroalcohol) in order i) to remove easily by-products and salts from CMS simply by filtration or by decantation; ii) to prevent gelatinization of starch granules; iii) to obtain a degree of substitution higher than that carried out in aqueous medium; iv) to increase product yield and reaction efficiency. According to an embodiment of the present invention, the functionalized starch is prepared under sub-optimal condition (i.e. temperature of the reaction is at 22° C., instead ≥40° C. as described in prior arts). At room temperature, the reactivity of reagent is low (or slowed down) and permitted the dispersing or penetration of the reagent within starch granules; In this case, the functionalizing reaction is uniform and not only on the surface of starch granules, but also inside starch granules which presents a structure more porous and composed predominantly the single helix V-type. However, the time of reaction is longer to complete the reaction of functionalization.

For food and pharmaceutical applications, the ethanol and isopropanol are preferably used, but synthesis is also possible with other solvents such as methanol, n-propanol, butanol, isobutanol, etc. or combination thereof.

An amount of 100 g of native starch is introduced in 1 L of ethanol (90%, v/v) containing sodium hydroxide at least 3.0 M. Then, an amount of 125 g of sodium monochloroacetate is immediately added to the medium at the room temperature. The reaction is performed during at least 10 h (or more), preferably 16 h under continuous stirring. During the carboxymethylation, some volumes of absolute ethanol are added in the medium in order to compensate the loss of ethanol evaporated, while maintaining the concentration of ethanol approximately between 80-90%.

At the end of the reaction, the precipitate is separated by filtration (or by decantation) and washed with an excess (~3 L) of ethanol 80% to remove the maximum of alkaline medium and by-products (mainly sodium hydroxide, sodium chloride, sodium glycolate, diglycolate or carboxymethyl ethyl ether, etc.). The neutralization is done under stirring by mixing the precipitate in 2 L of ethanol (80%) containing 5-10% (v/v) of organic acids (preferably glacial acetic acid). The neutralization process can be operated several times until obtaining a pH value between 6.0 and 7.0. Finally, the precipitate is collected and washed with 3 L of ethanol (80%) followed one more time in absolute ethanol before drying at 40° C. overnight to obtain the CMS powders.

Similarly, different quantities (100-150 g) of sodium monochloroacetate are used separately in identical preparation described above in order to obtain various DS.

1.2. Carboxymethylation of Corn Starch in Hydroalcoholic Media

Similarly, the carboxymethylation of corn starch (Hylon VII, National Starch, NJ, USA) is done as described previously for corn starch, but the time of reaction is at least 14 h, preferably 18 h.

1.3. Characterization of Carboxymethyl Starch
1.3.1. Determination of Degree of Substitution (DS)

The DS is defined as the average number of substituents per glucose unit (GU), the monomer unit of starch. Since each GU contains three hydroxyl groups, the DS can vary between 0-3.

The DS value is determined by titrimetric method. An amount of 5 g of CMS is dispersed in 100 mL of ethanol containing 3.5% hydrochloric acid (HCl) and stirred during 1 h at room temperature. The sample is collected by filtration and washed several times with ethanol 90% to remove the excess of HCl and one time with acetone before drying in oven at 40° C. for overnight. After drying the sample, an amount of 1 g of CMS (in acid form) is dissolved in 100 mL of distilled water and titrated with 0.05 M of standard sodium hydroxide to a neutral point. Each sample is run in triplicate.

For different quantities of sodium monochloroacetate (100-150 g), the DS is varied between approximately 0.25 and 0.55 and no significant difference between corn and potato starch is observed.

1.3.2. Fourier Transform Infrared (FTIR) Analysis

FTIR spectra were recorded on a Spectrum One (Perkin Elmer, Canada) instrument equipped with an UATR (Universal Attenuated Total Reflectance) device. The native and carboxymethyl starch (including carboxymethyl hydrolyzed starch) samples were tested under powder (20 mg) or tablet (400 mg) forms in the spectral region (4000-650 cm$^{-1}$) with 24 scans/min at a 4 cm$^{-1}$ resolution.

Figure 3:
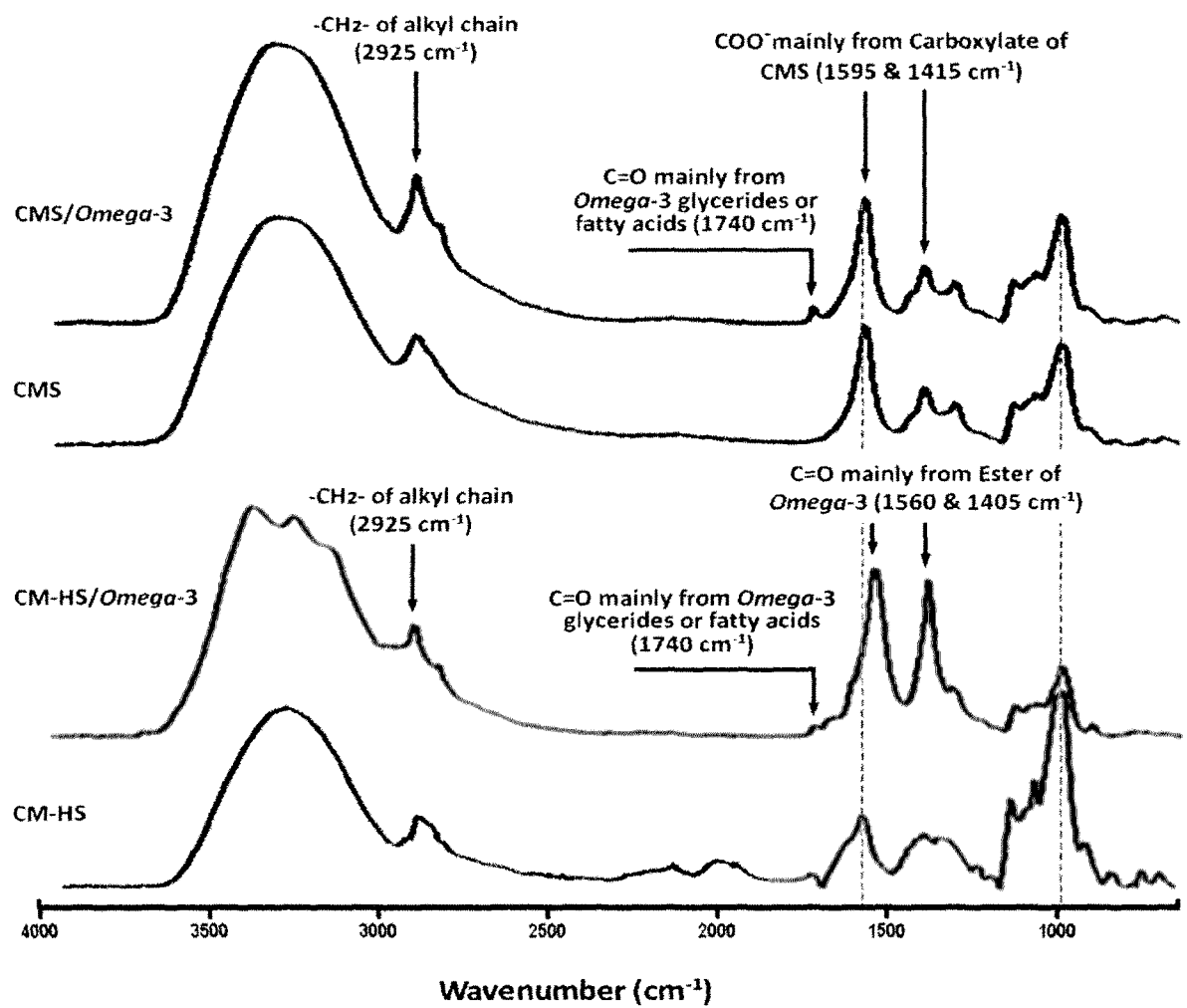
FIG. 3 illustrates FTIR spectra of carboxymethyl hydrolyzed starch (CM-HS) and of carboxymethyl starch (CMS) alone and complexed with Omega-3.

The FTIR analysis allows to confirm that the reaction occurred by highlighting the presence of carboxylate groups in the obtained powder. In fact, new absorption bands appear at 1595 and 1415 cm$^{-1}$ assigned to carboxylate (asymmetric and symmetric stretching vibrations) anions after carboxymethylation of starch (FIG. 3).

1.3.3. X-Ray Diffraction (X-RD) Analysis

The diffraction patterns of different tablet samples were recorded using a Siemens D-5000 Diffractometer (Munich, Germany) with a cobalt cathode operating in reflectance mode at wavelength 1.79 Å. The diffractograms, recorded between 5 and 50° for 2-theta angle, were treated using a Diffracplus software.

For native starch powder (FIG. 4), a predominant double helix B-structure is observed with a high order degree. This helix B-structure is characterized by the maxima of diffraction bands located at 5.7, 5.2, 3.9 and 3.7 Å (Ispas-Szabo, P., Ravenelle, F., Hassan, I., Preda, M., Mateescu, M. A. 2000. *Carbohydr. Res.*, 323, 163-175) whereas bands located at 6.8 and 4.5 Å are attributed to the V-type structure, but their diffraction intensities are low and diffuse.

Figure 4:
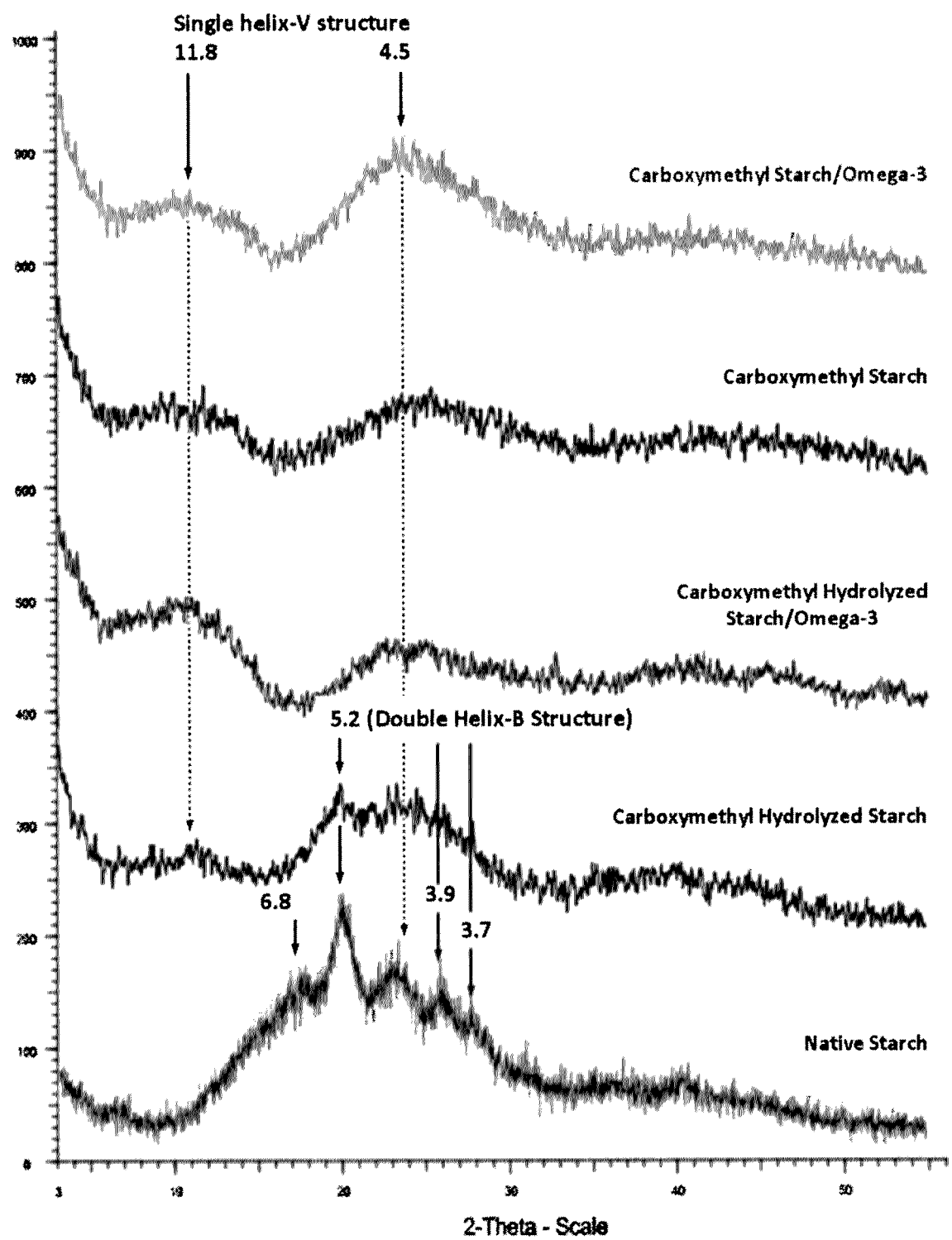
FIG. 4 illustrates X-Ray diffraction patterns of native starch and carboxymethyl starch (CMS and CM-HS) with and without complexed Omega-3.

After carboxymethylation of starch, almost all characteristic bands for initial helix B-structure are lost in diffractogram, except the band at 4.5 Å essentially attributed to the helix V-structure (FIG. 4). In addition, the diffraction band at 6.8 Å disappears and is replaced by a new band broader (suggesting a more amorphous character) observed at 11.8 Å, also related to a helix V-structure according to Bear (Bear, R. S. 1942. *J. Am. Chem. Soc.*, 64, 1388-1391).

In general, the carboxymethylation of starch induces the change of crystalline structure from double helix B- to single helix V-structure which presents two diffraction bands typically located at 4.5 and 11.8 Å. This single helix V-structure is characterized by a pronounced hydrophobic cavity which is responsible for the insertion of Omega-3 including triglycerides inside its structure with improvement on the solubility, dispersion and viscosity of Omega-3/CMS complex.

1.3.4. Scanning Electron Microscopy (SEM)

In order to highlight the differences between CMS synthesized in aqueous and in hydroalcoholic media, SEM is realized. For that purpose, CMS is prepared in identical conditions as previously described in the section «Carboxymethylation of Potato Starch in Hydroalcoholic Media», but water is used instead of ethanol as reaction medium. The DS is approximately 0.20.

The morphology and surface characteristics of CMS synthesized in aqueous and ethanol media are examined at various magnifications (100-1000) with a Hitachi S-3400N Variable Pressure SEM (JEOL Ltd., Tokyo, JP). The images are obtained with voltages of 10 kV and high vacuum.

For CMS synthesized in water medium (CMS-aqueous, FIG. 5), the SEM granules are small and fine, predominantly spherical (round with smooth surface), but size distribution is not uniform with range varying between 2.5-15 μm.

With regard of CMS synthesized in ethanol medium (CMS-ethanol), the morphology appeared completely different from that synthesized in aqueous environment. Indeed, CMS-ethanol granules in SEM micrographs are characterized by larger and greater particles (between 50-200 μm) with irregular shape and moderately smooth surface. In any case, CMS-ethanol granules present a size greater than CMS-aqueous suggested that there is a major change in CMS-ethanol, probably related to its high DS.

Example 2

Carboxymethylation of Hydrolyzed Corn Starch (CM-HS)

2.1. Synthesis of Carboxymethyl Hydrolyzed Corn Starch

To highlight the involvement and the behavior of CMS helix V-structure with BA, native starch is i) firstly hydrolyzed by sulfuric acid in order to reduce partially the chain length and to alter certain helical structures; ii) secondly, hydrolyzed starch (HS) is carboxymethylated and tested with various BA.

A quantity of 100 g of starch is dispersed in 1.0 L solution of $H_2SO_4$ 3M under stirring at 40° C. during at least 5 days. After hydrolysis, the starch suspension is washed by successive centrifugations in distilled water until the pH value reaches up to 7.0. The precipitate of hydrolyzed starch is collected by filtration and washed three times in an excess of acetone before being dried in an oven at 40° C. to obtain corresponding powder. The carboxymethylation of hydrolyzed starch is carried out similarly as mentioned for CMS.

2.2. Characterization of Carboxymethyl Hydrolyzed Starch
2.2.1. Degree of Substitution of Hydrolyzed Starch The determination of DS is done as described previously for CMS. The DS obtained for CM-HS is lower than that of CMS. In fact, the maximum DS of CM-HS is approximately 0.35 and even with the use of higher concentration (150 g) of monochloroacetate, no significant change is observed.

2.2.2. Fourier Transform Infrared (FTIR) Analysis of Hydrolyzed Starch

The analysis of CM-HS FTIR spectrum allows to confirm that the reaction occurred by highlighting the presence of carboxylate groups which are characterized by new absorption bands located at 1595 and 1415 cm$^{-1}$ assigned to carboxylate (asymmetric and symmetric stretching vibrations) anions after carboxymethylation of hydrolyzed starch (FIG. 3). However, their intensity is much less than that of CMS, which is in accordance with the results obtained from DS.

2.2.3. X-ray Diffraction Analysis of Hydrolyzed Starch

For carboxymethyl hydrolyzed starch (FIG. 4), almost all bands (3.7, 3.9 and 6.8 Å) are lost. Their crystallinity and intensity indicated a loss in the starch double helix B-structure by acid hydrolysis, particularly with the decrease of the main band located at 5.2 Å. In addition, a new band appeared at 11.8 Å but its intensity is low. These observations suggest that the double helix B-structure of starch is strongly affected by the acid hydrolysis leading probably a macromolecular arrangement to adapt a different organization and more stable single helix V-type structure.

Example 3

Preparation of Omega-3 Water-Soluble or Dispersible Solid Forms

For this assay, crude Omega-3 from Menhaden fish (Sigma, Saint Louis, MO, US) is used. According to the manufacturer, this source contains 20 to 31% (w/v) Omega-3 (octadecatetraenoic, eicosapentaenoic and docosahexaenoic) fatty acids as triglycerides.

3.1. Incorporation of Omega-3 in Carboxymethyl Starch

No native starch, nor hydrolyzed starch may form an inclusion complex with Omega-3 at higher concentrations (>10%, w/w), because Omega-3 can gelatinized starch. Even with a small quantity of Omega-3, the obtained powders present visible oil traces and it is impossible to compact them under tablet forms.

Preparation of Omega-3 Solid Powder Forms by Inclusion in CM-Starch

An amount of 5 g of Omega-3 oil is uniformly sprayed directly on the powder surface of native starch, hydrolyzed starch, CMS and CM-HS (5 to 15 g). This process is done similarly to the liquid fluid bed granulation method. During the process, the mixture is mildly stirred and aerated (with nitrogen or an inert gas) at room temperature, until the Omega-3 oil solution is completely combined within the starch. After aeration during 2 h, uniform powders are obtained without visible traces of oil. The resulting CMS/Omega-3 powders (hereto called Omega-3 water-soluble or dispersible powders) are thereafter left to stand at room temperature for stabilization in the dark for at least 48 h or at 37° C. during 24 h before use.

Omega-3 Tablet Dosage Forms

For tablet dosage forms, the Omega-3 water dispersible powders are obtained by direct compaction in a Carver hydraulic press (0.4-2.3 T/cm$^2$).

3.2. Characterization of CMS/Omega-3 Complex Powders

Different ratios of CMS and Omega-3 are tested and the ratio allowing a complete soluble or dispersibility in water is about 2:1, but may also include a wide variety of ratios depending of the nature of the preparation of Omega-3 and the type of functionalized CMS used. For example, according to an embodiment the ratio for Omega-3 and CMS is about 1:2 and according to another embodiment, the ration of Omega-3 and a partially hydrolyzed CMS may be 1:1.

3.2.1. Loading Capacity

Data analysis shows that the DS of CMS is a main factor that influenced the quantity of Omega-3 incorporated inside CMS (which is defined as loading capacity). Indeed, the higher the DS, the larger the Omega-3 quantity incorporated inside CMS. The explanation of this phenomenon can be based on the relation between DS and single helix V-structure. In fact, it is believed that at higher DS, more the double helices of starch are disorganized and adopt mainly the single helix V-structure, which lead consequently to an increase of the BA loading capacity.

For DS<0.2, the Omega-3 maximal loading capacity in CMS is about 10% (w/w). When compressing these complex powders to obtain the tablet form, there is overflowing of oil from the tablet. For DS superior to 0.25 or more, the loading capacity can reach up to 35% of Omega-3 with satisfactory mechanical properties (powders obtained without visible traces of oil and with no liquid overflowing when compressed under tablet forms).

3.2.2. Physicochemical Properties of Omega-3 Solid Powders 3.2.2.1. Dispersibility in Water of Omega-3 Solid Powders Different quantities (0.5-5 g) of CMS/Omega-3 complex are dispersed in 100 mL of water under stirring at room temperature. Solutions are stable and homogeneously dispersed in aqueous media without the well-known phase separation. However, an increasing viscosity and a reducing of limpidity of medium as a function of CMS/Omega-3 quantities added in water are noticed.

3.2.2.2. Compressibility of Omega-3 Solid Powders under Tablet Dosage Forms

For tablets obtained by direct compression from CMS/Omega-3 solid powders, no oil liquid overflowing or surrounding tablet is observed for compaction forces up to 1.6 T/cm2).

3.2.2.3. Stability of Omega-3 Solid Powders

Daylight Stability

Figure 5:
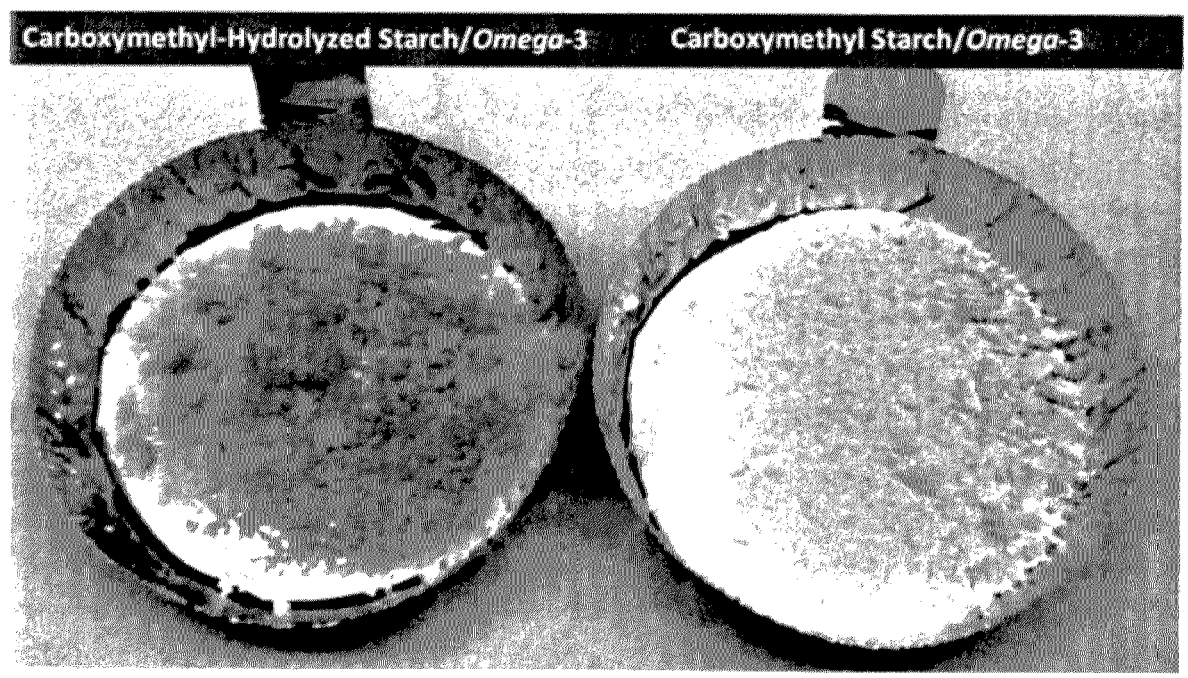
FIG. 5 illustrates light stability of Omega-3 complexed by CM-HS and by CMS (one week daylight exposure).

The test consists in exposing to daylight the CM-HS/Omega-3 and CMS/Omega-3 complex powders at the room temperature. After an exposure of up to one week, the color of the CM-HS/Omega-3 complex powders is changed from white to yellow indicating an oxidation phenomenon (FIG. 5). This is due to Omega-3 which probably remained outside of the helical cavity, because almost all helical structures of CM-HS are altered by hydrolysis with acid.

In contrast, no color change is observed for CMS/Omega-3 complex powders during the same period of exposure suggesting that Omega-3 are well integrated inside the CMS which presents an effective protection.

UV Light Stability

The test consists in irradiating directly different samples under an UV source (0.05 kGray/h) for increasing periods of time (0, 15, 30, 60 min and 5 h). Reactive oxygen species (ROS) generated by UV can oxidize Omega-3 and thus reduce its antioxidant activity. The protection properties are evaluated by electrolysis method as described by Le Tien et al. (Le Tien, C., Vachon, C., Mateescu, M. A., Lacroix, M. 2001. *J. Food Sci.*, 66, 512-516) with slight modifications.

An amount of 1 g of Omega-3 oil or CMS/Omega-3 powders is suspended in 100 mL of absolute ethanol saturated in NaCl, under gentle stirring. After homogenous dispersion, a volume of 3 mL of mixture (corresponding approximately to 10.5 mg of Omega-3) is introduced in an electrolysis cell under continuous current (400 Volts, 10 mA for 1 min at room temperature) using a power supply (Bio-Rad, model 1000/500). Similar preparation is performed for Omega-3 oil (10.5 mg) extracted from commercial soft-gel capsules. Then, an amount of 1 mL of electrolyzed sample is withdrawn from electrolysis cell and introduced in 2 mL of DPPD (N,N-diethyl-para-phenylenediamine) solution (25%, w/w). The retained antioxidant capacity of Omega-3 is determined at 515 nm and calculated accordingly to the equation:

Scavenging (%)=100−[(OD sample/OD control)× 100]

Where OD control (control optic density) represents the OD of ethanol solution with electrolysis in absence of any sample (ascribed to 0% scavenging).

Figure 6:
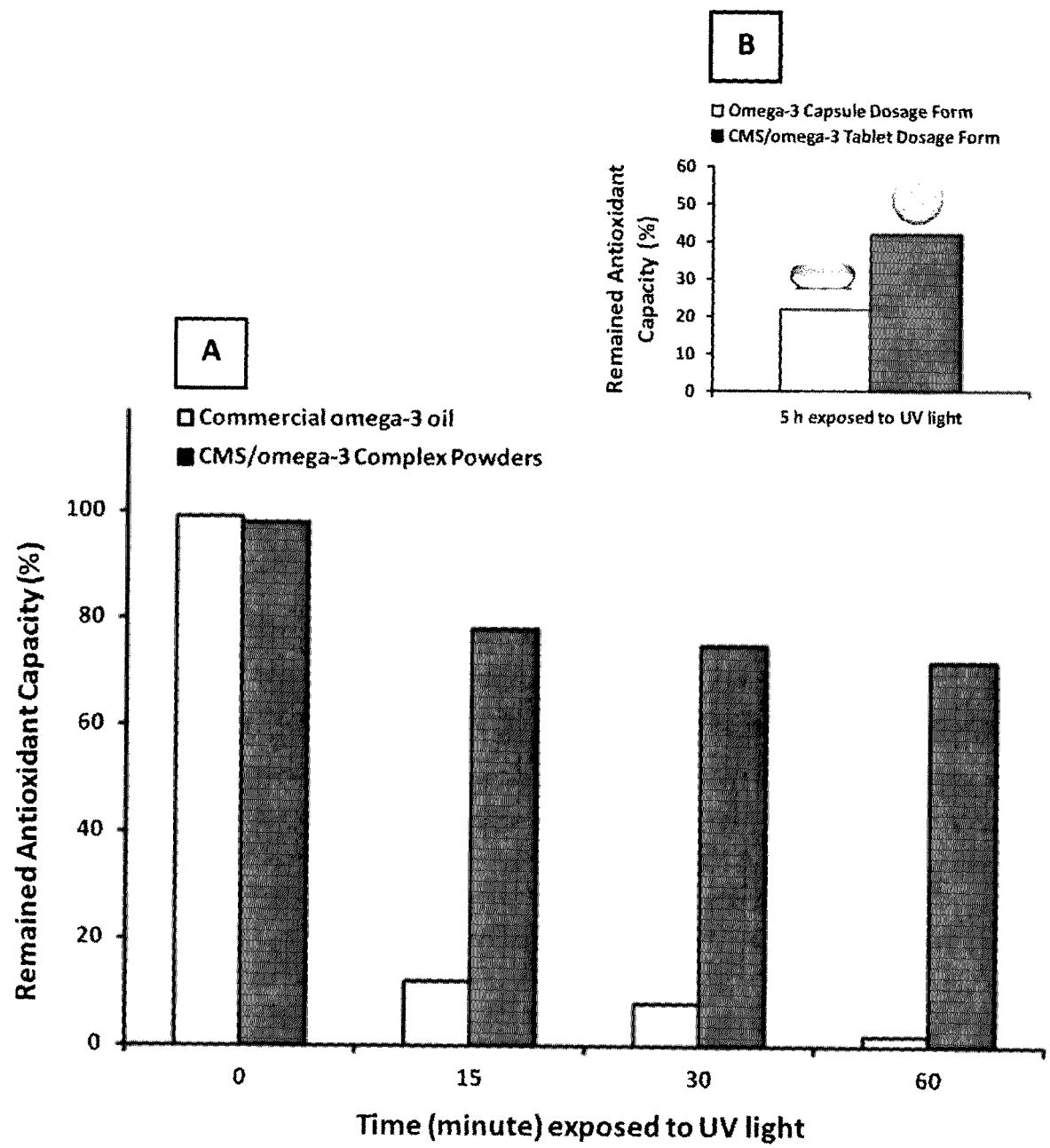
FIG. 6 illustrates the stability expressed as remaining antioxidant capacity of commercial liquid Omega-3 oil and of CMS/Omega-3 inclusion complex powders (A) and of formulated (B) as gel capsule and monolithic tablet (CMS/Omega-3) after UV exposure (5 h).

The relative antioxidant capacity of CMS/Omega-3 powder is compared with Omega-3 oil extracted from commercial soft-gel capsules after similar exposure the UV (FIG. 6). The Omega-3 oil from commercial capsules showed a loss of about 90% of its antioxidant capacity after only 15 min exposure to an UV source, whereas for the Omega-3 powders (CMS/Omega-3 complex) the loss is less than 25% of antioxidant after 1 h UV exposure.

When the whole commercial capsule with Omega-3 is exposed to UV for 5 h, the remained antioxidant capacity is of 25% whereas monolithic tablets of CMS-Omega-3 after similar exposure presented more than 40% antioxidant capacity. This indicates that Omega-3 monolithic tablet possesses a protection more effective than that afforded by soft-gel capsule.

3.2.2.4. Degradation of CMS/Omega-3 Tablet Dosage Form by Alpha-Amylase

The assays are carried out as described by technical procedure of Sigma-Aldrich for Enzymatic Assay of α-Amylase (EC 3.2.1.1) with modifications as follows: native starch, CMS, CMS/Omega-3 tablet (300 mg) are incubated in 50 mL of SIF (pH 6.8 at 37° C. and 100 rpm) containing 25 U/mL (1250 Units in total) of Alpha-amylase according to USP (United States Pharmacopeia). At different time intervals, an amount of 2 mL of samples are withdrawn from SIF which is introduced in tube containing 1 mL of DNS (3,5-Dinitro salicylic acid) reagent solution. After heating during 15 min, the tubes are cooled down on ice bath and 9 mL of water are added. The intensity of the orange-red color developed in the medium (due to the reduction of DNS by maltose) is spectrophotometrically measured at 540 nm.

Although a slight resistance to amylase attack is observed for CMS and CMS/Omega-3 (due to starch carboxymethylation), the differences are minor. In any case, enzymatic degradation of CMS (with or without Omega-3) after 4 h in SIF may be useful, because intestinal Alpha-amylase can contribute to a more efficient release of Omega-3 bioactive agent from the CMS monolithic tablets in intestinal tract in the controlled manner.

3.2.2.5. Dissolution Assay of Omega-3 Tablet Dosage Form

Dissolution kinetics are followed with a Distek apparatus according to USP (method 32). Tablets are placed in 50 mL simulated gastric fluid (SGF, pH 1.5) during 2 h and then transferred in 50 mL of simulated intestinal fluid (SIF, pH 6.8). At different intervals (1, 2, 4, 6, 8 and 10 h), the tablet samples are removed from dissolution media. Then for each sample, an aliquot of 3 mL of dissolution fluid is withdrawn and diluted with 3 mL of iso-octane. The mixture is centrifuged at 1000 g for 2 minutes, filtered and absorbency measured with an UV (Ocean Optics Spectrophotometer) at 230 nm. Standard curve is established with different concentrations of Omega-3 from 0 to 100 μg/mL iso-octane.

The commercial Omega-3 oils in soft gel capsules are naturally insoluble in aqueous fluids. When subjected to the dissolution assays, these commercial capsules remained at the surface of SGF (can float for several hours). Generally, no release of Omega-3 is observed within 2 h. When the incubation is continued in the identical conditions, the capsule is finally broken after 10 h and completely released Omega-3 oil liquid which always remained on the surface of SGF (FIG. 1).

Figure 7:
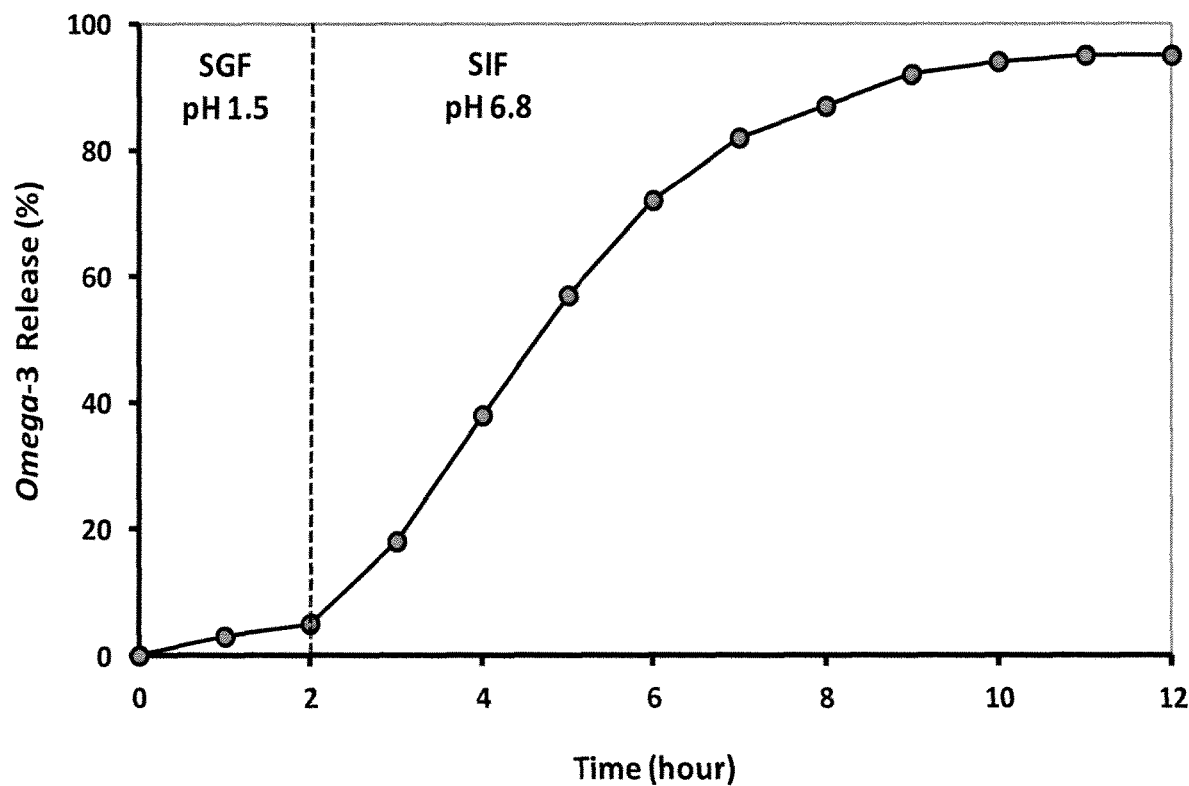
FIG. 7 illustrates the release profile of Omega-3 from CMS/Omega-3 tablet dosage form.

Differently, no floating or swelling are observed for water dispersible CMS/Omega-3 tablets with only some minor amounts of Omega-3 released in the SGF (FIG. 7). The non-swelling is probably due to the presence of large quantities of Omega-3 which confer a hydrophobic character to the tablet limiting its hydration and the release of Omega-3. Furthermore, the CMS matrix, due to the protonation of carboxylate to carboxylic groups in gastric acidity will stabilize the tablet and prevent Omega-3 release in the SGF.

In SIF, a gradual release of Omega-3 with a complete liberation after 10 h is observed (FIG. 7). This sustained release in SIF (neutral pH) is mainly controlled by the access of intestinal fluid within the CMS/Omega-3 tablets due to deprotonation of carboxylic (—COOH) acid (sparingly soluble form) in more soluble carboxylate (—COO$^-$) groups. This dissolution profile fits well the needs for a better absorption improving thus the efficiency of CMS/Omega-3 tablets obtained from the present invention.

3.2.3. FTIR Analysis of Omega-3 Solid Powder Forms

CMS/Omega-3 Complex

Referring to FTIR spectrum of CMS/Omega-3 complex (FIG. 3), an increase of the absorption intensity of the band at 2925 cm$^{-1}$ is observed. This increase is clearly related to alkyl chains of Omega-3 present in the inclusion complex. In addition, a new absorption band appeared at 1740 cm$^{-1}$ assigned mainly to the (C═O) groups from Omega-3 (glycerides or free fatty acids). Surprisingly, no change is observed for other bands, particularly those at 1595 and 1415 cm$^{-1}$ which are assigned respectively to asymmetric and symmetric stretching vibrations of carboxylate groups of CMS.

CM-HS/Omega-3 Complex

Similar observations are noticed for CM-HS/Omega-3 inclusion complex (FIG. 3): i) an increase of intensity for band at 2925 cm$^{-1}$ and ii) an appearance of new band at 1740 cm$^{-1}$. Additionally, there are shifts of absorption bands located at 1595 to 1415 cm$^{-1}$ to low wave numbers i) from 1595 to 1560 cm$^{-1}$ and ii) from 1415 to 1405 cm$^{-1}$, respectively. These shifting phenomena observed for CM-HS/Omega-3 inclusion complex can be due to the stretching vibrations of (C═O) from mainly Omega-3 glyceride esters rather than to (C═O) of carboxylate (COO$^-$) groups from CM-HS.

There may be an overlap of (C═O) bands from ester of Omega-3 and from carboxylate of CM-HS. However, band intensities are significantly different between untreated (without Omega-3) CM-HS and Omega-3/CM-HS.

These observations are in line with the helical-V structure of hydrolyzed starch, which is almost altered by acid hydrolysis. In this case, only a small amount of the Omega-3 is incorporated inside CM-HS helix V-structure, whereas most of the Omega-3 fatty acids probably remained outside the helical cavity.

In contrast, no significant changes (intensity or shifts of absorption bands ascribed to carboxylate groups) are observed for CMS/Omega-3 complex. These FTIR data suggested that most of the Omega-3 is incorporated inside the helical-V structure of CMS which explains why the CMS/Omega-3 inclusion complex presents a greater solubility and dispersibility compared with other inclusion complexes, including native starch/Omega-3.

3.2.4. X-Ray Diffraction of Omega-3 Solid Powder forms

As previously mentioned, the carboxymethylation of starch induces the change of crystalline structure from double helix to single helix V-type. This single helix V-structure is characterized by a deep hydrophobic cavity which is responsible for the insertion of Omega-3 including triglycerides inside its single helical cavities.

Similar to X-ray pattern profile of CMS (FIG. 4), the CMS/Omega-3 complex showed bands typically attributed to helix V-structure located at 4.5 and 11.8 Å. Furthermore, all these bands suggested a significant increase of the crystallinity, more important than CMS (without Omega-3). These data also suggest that Omega-3 fatty acids incorporated inside the CMS helix V-cavity can generate a structure more ordered than that of CMS without Omega-3.

With regard to the CM-HS/Omega-3 complex, there are also major changes (FIG. 4). For the region between 15 and 30 degree (2-theta), almost all bands disappeared and are replaced by a single diffused band at 4.5 Å with a low intensity suggesting an amorphous structure. In parallel, a significant increase of intensity for a broader band located at 11.8 Å is observed. These data indicate a close relationship between Omega-3 and helix V-structure of starch which is characterized by two bands located at 11.8 and 4.5 Å.

When comparing the two inclusion complexes, the structure of Omega-3 incorporated inside CMS is more organized and more stable than that of Omega-3 inside CM-HS, because the majority of helical structures of CM-HS are altered by acid hydrolysis. It is of interest to mention that Omega-3 can play an important role in the stabilization of CMS which improve the crystallinity of CMS without alteration of its physical properties (solubility, dispersibility, viscosity, etc.).

3.2.5. Scanning Electron Microscopy of Omega-3 Solid Powder Forms

Figure 8:
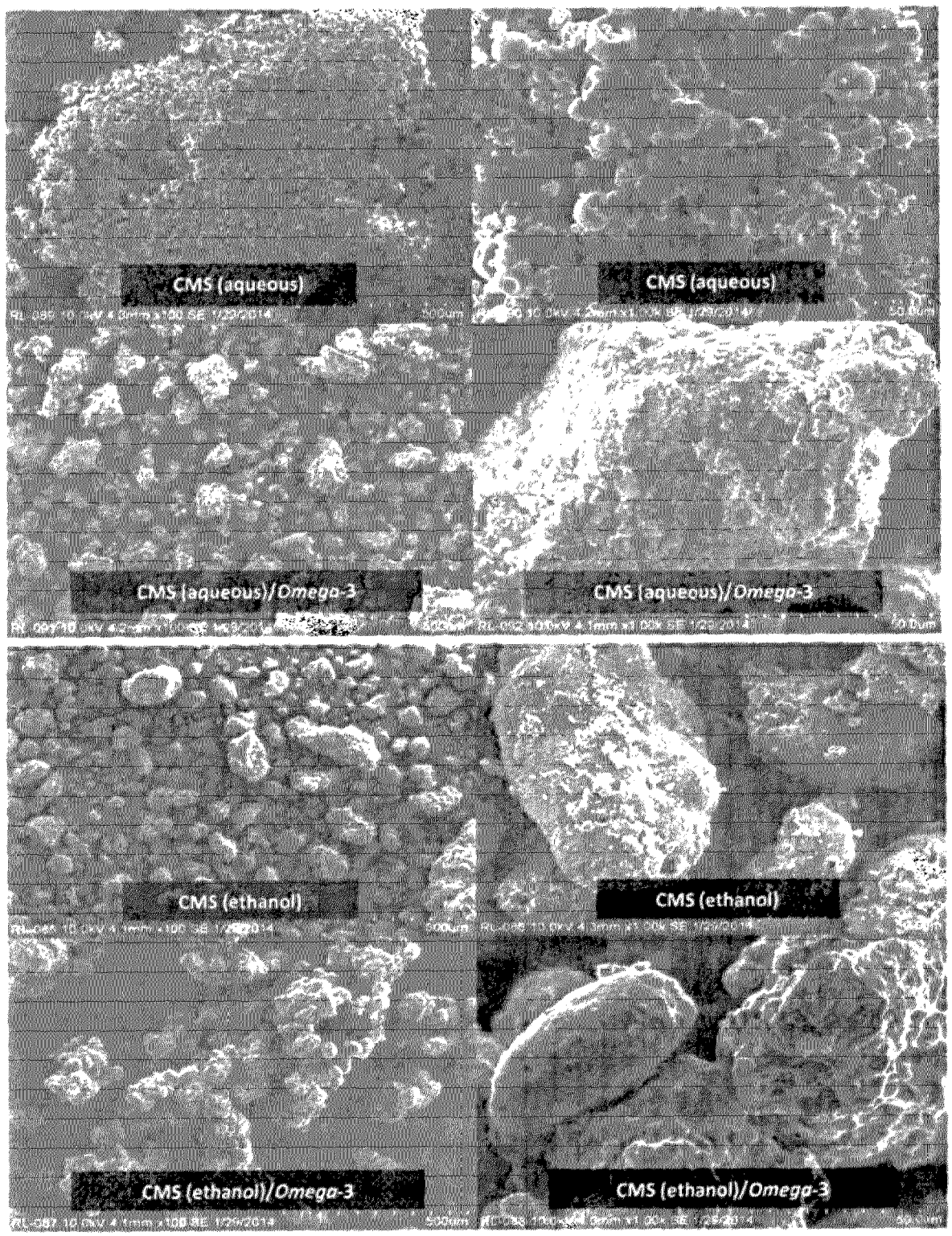
FIG. 8 illustrates Scanning Electron Microscopy of free CMS synthesized in aqueous and ethanol medium and their corresponding complexes with Omega-3 (at 100 and 1000 magnification).

Referring to FIG. 8, the morphologies and surface characteristics of CMS/Omega-3 obtained with CMS synthesized in aqueous and ethanol media present different appearances.

When Omega-3 are incorporated in CMS obtained in aqueous medium, the SEM granules are completely changed. In the presence of Omega-3, the small granules from CMS-aqueous lose their smooth surface and spherical shape to become larger and moderately rough with various size (10-25 µm).

With regard of Omega-3 incorporated in CMS synthesized in ethanol, the granule aspect appeared fairly uniform almost keeping the size but with rougher surfaces. Furthermore, these granules are connected to each other and disposed in chain forms.

In both case, the introduction of Omega-3 induces changes in the CMS granule morphology which suggest that there is rearrangement or reorganization of CMS structure in order to adopt an inclusion complex more stable and more organized, as revealed by FTIR and X-ray Diffraction analyses.

3.2.6. Iodine Test

Iodine can interact with starch inducing a formation of blue colored inclusion complexes. This is due to the iodine included in the central channel of the amylose helix. When the channel is occupied, no color change is observed (Exarhopoulos, S., Raphaelides, S. N. 2012. *J. Cereal Sci.*, 55, 139-152). Similar behavior is observed for our carboxymethyl starch and for this reason, the iodine test is used as a probe in order to highlight the localization of Omega-3 inside or outside of CMS cavity. A volume of 300 µL of iodine (2.0%, KI and 1.0% (w/v) $I_2$ in distilled water) is added to different solutions (60 mL) each containing 0.5% (w/w) of various samples at room temperature.

The results (FIG. 9) revealed that the CMS solution without incorporation of Omega-3 (control) developed a blue/violet color, indicating the formation of CMS/iodine inclusion complex.

In contrast, no color is observed for the solution containing the CMS/Omega-3 inclusion complex suggesting that fatty acids and/or glycerides of Omega-3 are located inside the CMS single helix cavities and prevented the access of iodine.

It is of interest to mention that no visible oil traces is observed on the surface of the solution. This observation indicates that probably almost all forms of Omega-3, including triglycerides, have been involved in the formation of the CMS/Omega-3 inclusion complex. To confirm whether triglycerides from Omega-3 can induce the complex formation with CMS, Tristearin (glyceryl tristearate derived from glycerol and three units of stearic acid) is selected to be incorporated in CMS. The preparation is carried out in conditions similar to those described previously in the section of incorporation of Omega-3 in CMS, with slight modification.

Figure 9:
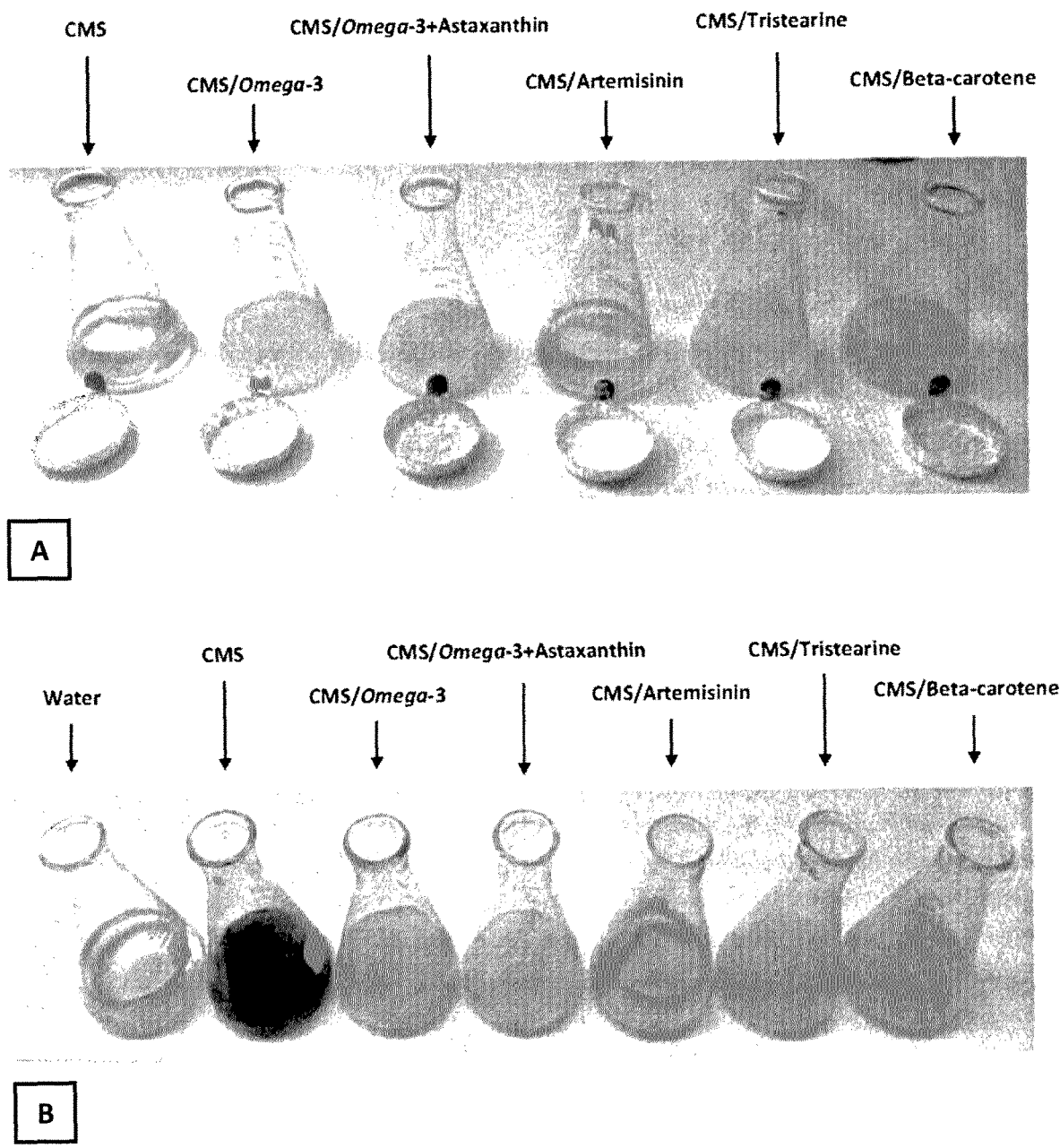
FIG. 9 illustrates different bioactive complexes with CMS in the absence (A) and in the presence (B) of iodine, with CMS as control.

Indeed, an amount of 1 g of Tristearin is dissolved in 10 mL of hot acetone and introduced directly in the beaker containing 3 g of CMS powders, under gentle stirring at 60° C. The incorporating process is continued until the acetone in the beaker is completely evaporated. The resulting powders are thereafter left to stand for stabilization in the oven for at least 24 h prior to carrying out the iodine test. The results show that no development of any color is observed in the CMS/Tristearin complex solution, suggesting Tristearin is included in the CMS helical cavity (FIG. 9).

Although the inclusion complex formation between starch and free fatty acids or monoglycerides has been reported, no report until now had showed that lipids with larger size such as triglycerides can be incorporated inside starch, particularly with modified starch such as carboxymethyl starch.

In comparison to mono- and di-glycerides, the triglycerides possess a larger size with a steric structure inaccessible or unfavorable for their insertion inside the double helical cavity of starch. However, when starch is modified by carboxymethylation by method described in the present invention, the double helix-B form is changed to the single helix-V form which seems to present a more hydrophobic and larger channel compared with the double helix form. In this case, the incorporation of triglycerides inside the helix V-structure is more favorable than that in the double helix.

According to an embodiment, the inclusion in CMS described here, for the first time, is not limited only for BA under triglyceride forms, but also for other BA with more complex structure such as Cholecalciferol, Artemisinin, Phytomenadione, etc. or mixture thereof which are also possible.

Example 4

Incorporation of Alpha-Linolenic Acid in Carboxymethyl Starch

Fatty Alpha-Linolenic Acid (ALA) is an extract from the flax plant seeds and rich in Omega-3 which is benefic for health. ALA is mainly commercialized under liquid oil forms (flaxseed oil). An ALA water dispersible solid form is prepared under identical conditions described for preparation of Omega-3.

Example 5

Incorporation of Liposoluble Vitamins in Carboxymethyl Starch Vitamin D (Cholecalciferol)

Like other BA, cholecalciferol is insoluble in water, but soluble in ethanol or acetone. For incorporation inside CMS helical-V cavity, it is necessary first to solubilize the cholecalciferol in ethanol (or acetone, 1.5 mg/10 mL corresponding to 60000 IU) until obtaining a clear colorless solution. Then, the solution is sprayed directly on the powder surface of CMS (1 g) in the same conditions and process as described for preparation of Omega-3.

Other Vitamins

Other Vitamins such as vitamin A (trans-retinol), vitamin E (tocopherol) and vitamin K (phytomenadione) can be similarly prepared as described for cholecalciferol.

Example 6

Combination of Multiple Bioactive Agents in Carboxymethyl Starch 6.1. Preparation of Astaxanthin Water-Soluble or Dispersible Powder Forms According to another embodiment, the BA present in the following examples can be incorporated alone (separately as described previously), but it is equally possible to combine two or more BA such as Omega-3 or ALA with Astaxanthin or mixture thereof. The BA can be included together in CMS or separately and their water dispersible powders can be mixed for further uses.

6.2. Astaxanthin

Astaxanthin, a natural extract of dried *Haematococcus pluvialis* microalgae, is an antioxidant with a potent and beneficial effect on health. Astaxanthin possesses a low availability, like other carotenoids. A part from incomplete release from various matrices (foods), the low bioavailability of Astaxanthin is probably due to its dissolution limitation in the gastrointestinal fluids. Another factor suggested to limit Astaxanthin absorption is a moderately low capacity of incorporation into bile micelles. However, its bioavailability can be enhanced in the presence of a lipid. In this case, it is of interest to combine Astaxanthin with Omega-3 (or with ALA or mixture thereof).

An amount of 50 mg of Astaxanthin is introduced slowly in 5 g of Omega-3 oil liquid (or ALA or mixture thereof) under gentle stirring at room temperature, until obtaining a homogenous solution. For incorporation in CMS, the preparation is done as previously described for Omega-3, with the mixture of Omega-3 and Astaxanthin.

6.3. Beta-Carotene

Similarly, the preparation of Beta-Carotene with Omega-3 (1%, w/w) combination is carried out under identical conditions, as described for Astaxanthin.

6.4. Multiple Bioactive Agents

Following the same principle, it is possible to combine multiple BA water dispersible powder forms. For instance, Beta-Carotene, Astaxanthin, Lutein, Zeaxanthin, Lycopene and Resveratrol can be combined with Omega-3 oil liquid (or ALA or mixture thereof) as described for Astaxanthin.

Example 7

Preparation of Bioactive Agents-Based Drugs Water-Soluble or Dispersible Solid Forms Similarly, BA-based drugs are prepared in identical conditions as described previously for Omega-3. However, it is of interest to mention that certain BA-based drugs are only available under solid state such as Artemisinin, because of their insolubility and instability in aqueous media.

7.1. Incorporation of Artemisinin Water-Soluble or Dispersible Powder Forms

Artemisinin is insoluble in either water or oil, but soluble in certain pure solvents (i.e. acetone). In this case, it is important to dissolve first the Artemisinin BA with suitable and acceptable solvents such as acetone or mixture of acetone with alcohol (i.e. ethanol). Indeed, an amount of 1 g of Artemisinin is dissolved in 20 mL pure acetone (or mixture ethanol/acetone, 1:2, v/v) at 40° C. until obtaining a clear colorless solution.

For incorporation in CMS, the Artemisinin solution is sprayed directly on the powder surface of CMS (ratio of Artemisinin/CMS, 1:2 w/w) in the same conditions as described for preparation of Omega-3.

7.2. Dissolution Assay of Artemisinin Water Dispersible Monolithic Tablet 7.2.1. Dissolution Assay Parameters Water dispersible CMS/Artemisinin (600 mg, 12.5 mm diameter) monolithic tablets containing 200 mg of Artemisinin are obtained by direct compression of powders (2.3 T/cm² in a Carver hydraulic press). The kinetics of drug release are recorded using a Distek dissolution 2100A paddle system (100 rpm, 37° C.). The dissolution is followed in simulated gastric fluid (SGF, pH 1.5) for 2 h and then in simulated intestinal (SIF, pH 6.8) fluid, as referred by USP Method 32.

7.2.2. Dosage of Artemisinin using 2,2'-azinobis(3-ethyl-benzothiazoline-6-sulfonic acid)

Artemisinin release in the media is measured by spectrophotometry using 2,2'-azinobis(3-ethylbenzothiazoline-6-sulfonic acid, ABTS) as chromogenic reagent. Indeed, this method consists in using the chromogenic ABTS (initially colorless) reagent that will be oxidized by the endoperoxide of Artemisinin in acidic medium to form a radical cation (colored ABTS•+). The generated ABTS•+ color is directly proportional to the concentration of Artemisinin present in the medium and absorbency measured at 734 nm.

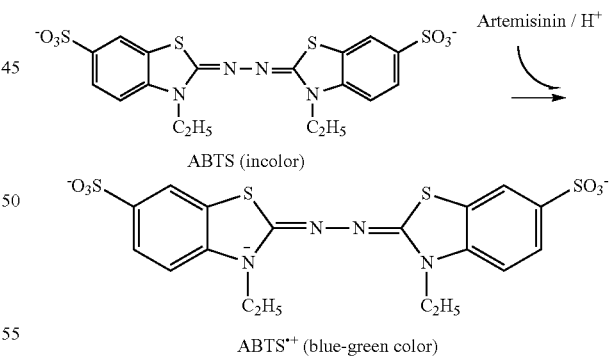

Oxidation of ABTS in ABTS•+ radical cation by Artemisinin endoperoxide in strong acid ($H_2SO_4$) medium.

7.2.3. Artemisinin Release Profile

Dissolution assays are followed with a Distek apparatus according to USP (method 32). Tablets are placed in 100 mL simulated gastric fluid (SGF, pH 1.5) during 2 h and then in 100 mL simulated intestinal fluid (SIF, pH 6.8). At different intervals (1, 2, 4, 6, 8 and 10 h), tablets are withdrawn from dissolution medium and a volume of 5 mL of ABTS diammonium salt (approximately 5 mM) is added. To start the reaction, an amount of 5 mL of concentrate $H_2SO_4$ is slowly introduced and incubate for at least 12 h before measuring at 734 nm. Standard curves are established with different concentrations of Artemisinin from 0 to 100 mg/100 mL for each medium SGF and SIF.

Figure 10:
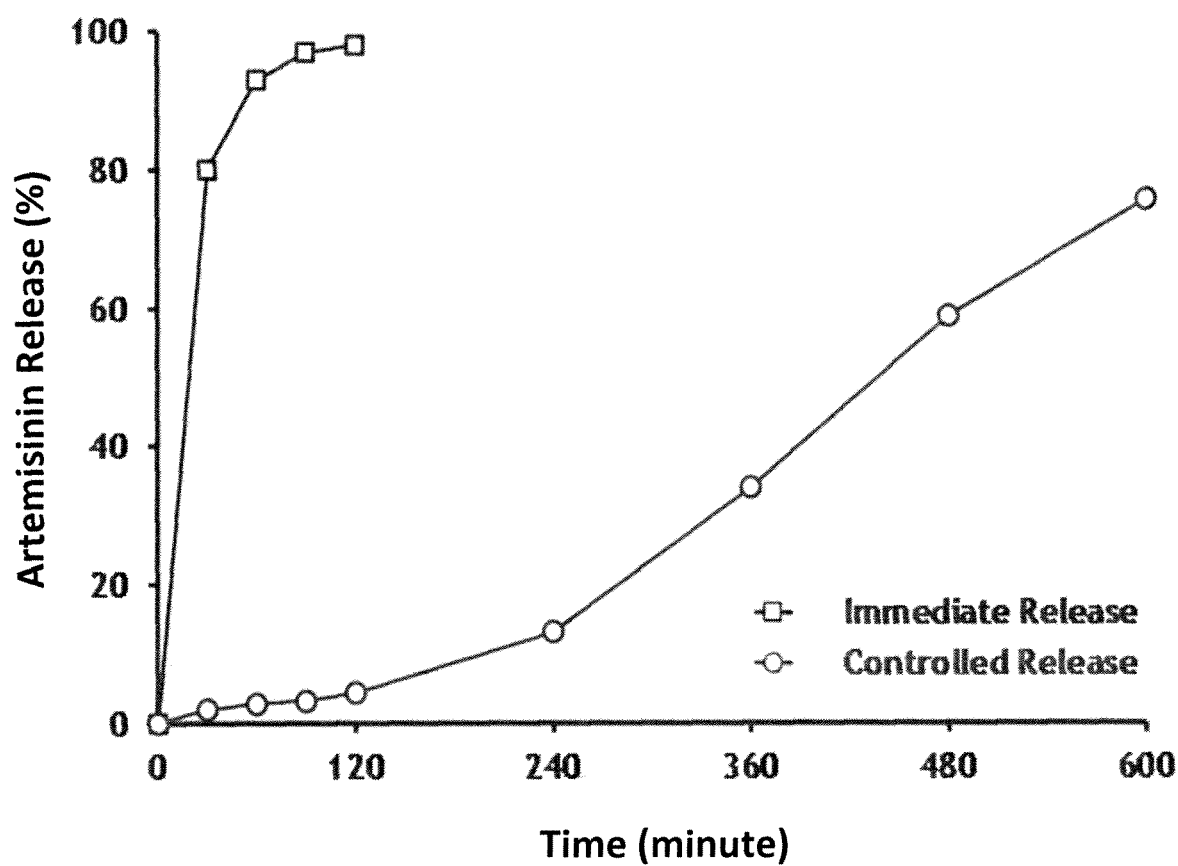
FIG. 10 illustrates the release profile of Artemisinin inclusion complexes with CMS formulated as monolithic tablets in the absence (controlled release) and in the presence of disintegrating agent (immediate release).

The Artemisinin dissolution pattern (FIG. 10) showed that no significant release of active principle occurred in SGF, whereas in SIF, a sustained release is observed with the content of Artemisinin completely liberated after 10 h.

When a disintegrating agent such as Croscarmellose sodium (cross-linked sodium carboxymethylcellulose, about of 100 mg) was added to the formulation of CMS/Artemisinin inclusion complex, the Artemisinin active principle was rapidly released from monolithic tablet in about 90 minutes. This immediate release formulation is useful to provide a rapid action required for fast relief.

7.2. Incorporation of Clopidogrel Water Dispersible Powder Form

Usually, Clopidogrel is commercialized under Clopidogrel bisulfate form. In a free base form, Clopidogrel (pKa 4.5) is an oily substance which is relatively unstable under increased moisture and temperature. In this case, it is of interest to use Clopidogrel under oil liquid form (no addition of sulfate salt) to incorporate inside CMS. The CMS/Clopidogrel inclusion complex seems more suitable for reducing side effects than Clopidogrel bisulfate form. Furthermore, the inclusion of Clopidogrel inside CMS can improve its solubility and bioavailability, thus enhancing its efficiency as API.

The preparation of CMS/Clopidogrel inclusion complex can be carried out in the same conditions as described for preparation of Omega-3. The ratio CMS/Clopidogrel is preferably about 1:1 (w/w) and aeration for stabilization is operated at room temperature in the dark for at least 48 h before use.

Example 8

Enhancing the Capacity of Functionalized Starch to Complex with BA 8.1. Factors Influencing on the Effectiveness of Functionalization Reactions in a Solvent-Water Media 8.1.1. Sources of Starch and Amorphous/Crystalline Regions In the present invention, different sources of starch can be used as starting materials such as corn starch, potato starch, pea starch, rice starch, bean starch, wheat starch, etc. or combination thereof. Depending on the source of starch, the ratio of amylose and amylopectin can vary. The amylopectin is considered responsible for the crystalline structure (A- and B-type) of starch, whereas the amorphous parts are related to the distribution of the ramifying (branching) points. These crystalline and amorphous regions may have an important impact on reactivity of functionalization process. Generally, the functionalizing agent is more reactive in the amorphous regions than in the crystalline structures which are more stable due to interchain interactions. Consequently, these variations affect reactivity and occur among differing botanical sources of starch, but also within a given population of a single source.

8.1.2. Structure of Starch Granules

The starch granule microstructure may also affect the reactivity of functionalization. The presence of pores at the surface of starch granules favors the diffusion of functionalizing agents into the granule matrix through lateral channels and interior cavities. In any case, pores and channels facilitate reagents to penetrate into the granule matrix and permit to obtain more uniformly functionalized and more effective starch products.

8.1.3. Size of Granules

Starch granule size may have an impact on the degree of substitution. Smaller granules contribute a greater surface area for reaction on an equal starch weight basis, when compared with larger granules. In the case of small granules, the exposed surface of contact with functionalizing reagents is higher and functionalization reaction is more effective.

8.1.4. Physicochemical Properties Functionalizing Agents 8.1.4.1. Nature of Reagent The nature of functionalizing agent is also an important factor. For hydrophilic reagents (i.e. sodium monochioroacetate), the reactivity is more effective than those with hydrophobic nature (1-octenyl succinic anhydride).

8.1.4.2. Size of Reagent

Generally, the reagents of large sizes hardly penetrate into the granule (due to the steric hindrance) and are lesser effective than those with small size.

8.1.4.3. Reactivity of Reagent

The highly reactive reagents react rapidly and predominantly at external granule surfaces. In contrast, slower reacting reagents can penetrate inside the starch granules and generally provide more uniform reaction patterns.

8.1.5. Type of Functionalization

Certain types of functionalization reactions are less rapid than the others. For instance, the reagents of the etherification are generally lesser reactive and the reaction is slower than the esterification.

8.2. Partially Hydrolyzed Starch

Another unique aspect in the present invention is to overcome these limiting factors. In order to convert double helices more effective in single V-helix with large center channel (hydrophobic cavity) and to increase the solubility of functionalized starch, it is of interest to partially hydrolyze starch just prior to the reaction of functionalization of starch. The partially hydrolysis of starch allows to:

- create more pores on the surface of starch favoring thus the penetration of reagents into starch granule; thus more porous starch granule can improve the capacity of BA inclusion;
- reduce crystalline regions (lesser interchain interactions) yielding more effective the functionalization reaction;
- diminish starch granule size and increasing thus the surface areas exposed to the contact with functionalizing reagents;

In addition, the reaction of functionalization is preferably operated:

- under sub-optimal conditions (i.e. temperature 22° C. instead ≥40° C.) to slowdown the reactivity of reagent and to facilitate the dispersing or penetrating the reagent into starch granules; In this case, the time of reaction is more longer;
- using reactive reagents of moderate reactivity (i.e. chloroacetate for carboxymethylation of starch by etherification) and small size in order to obtain a uniform functionalization, not only at the surface, but also inside starch granule;
- in water/alcohol media such as water with propanol, isopropanol, isobutanol, etc. and preferably in isopropanol (or isopropyl alcohol). The use of fatty alcohol (or alcohol with long chain such as 1-dodecanol) is possible and can gelatinize starch and minimize secondary (non-specific) reactions. Since the alkyl chain of fatty alcohol can lodge in the starch hydrophobic cavity during the functionalization reaction, this phenomenon can improve the effectiveness of the conversion from double helices in single helix, and enhance the cavity diameter of single helix V-structure.

Example 9

Carboxymethylation of Partially Hydrolyzed Starch

There are several methods to partially hydrolyze starch based on physical (i.e. gamma-irradiation), chemical (sulfuric acids) or enzymatic (isoamylase) processing or combination thereof. In the present embodiment, an enzymatic process without gelatinization of starch is preferably used. In this case, the hydrolysis of starch is carried out directly on starch granules.

For hydrolysis enzymatic procedure, numerous enzymes can be used such as alpha-amylase, beta-amylase, amyloglucosidase, isoamylase or combination thereof.

9.1. Partially Hydrolysis of Starch Using Amyloglucosidase

In the present invention, it is preferable to use amyloglucosidase (EC 3.2.1.3, also called glucoamylase or gamma-amylase or glucan 1,4-α-glucosidase), because this enzyme is capable to hydrolyze the alpha-D-(1,4) glucosidic bonds from non-reducing ends of the polysaccharides chains. According to *Nomenclature Committee of the International Union of Biochemistry and Molecular Biology* (NC-IUBMB), most forms of the enzyme can hydrolyze 1,6-alpha-D-glucosidic bonds when the next bond in the sequence is 1,4- and, some preparations of this enzyme, hydrolyze 1,6- and 1,3-alpha-D-glucosidic bonds in other polysaccharides.

For instance, an amount of 200 g of native corn starch (Hylon V, National Starch, NJ, USA) is hydrated under mild stirring in 2 L of distilled water to give a 10% (w/v) solid contents. Thereafter, an amount approximately of 200 AG (from *Rhizopus* sp) units/g of starch is added in the medium, always under mild stirring. The reaction is performed at room temperature (22° C.) and the pH 6.5-6.8. After at least 12 h and preferably 18 h, a volume of 1 L of ethanol is added to stop the reaction and to accelerate the precipitation of starch which is filtered and dried at 40° C. until for the next utilization.

9.2. Carboxymethylation of Partially Hydrolyzed Starch (PHS) Obtained by Amyloglucosidase Processing The carboxymethylation of PHS is similar with that previously described in Example 1 with slight modification. Indeed, an amount of 100 g of PHS was introduced in 1 L of solution of isopropanol/water (85/15, v/v) containing sodium hydroxide at least 3.0 M. The suspension was maintained under strong stirring to disperse starch and at high alkalinity to degrade completely the enzyme, if some traces remained. After obtaining a homogenous suspension, an amount of 125 g of sodium monochloroacetate was added to the medium and the reaction was continued for at least 18 h (or more), at room temperature (22° C.) under mild stirring.

At the end of the reaction, the precipitate is separated by filtration (or by decantation) and washed with an excess (~3 L) of methanol or ethanol 80% to remove a maximum of alkaline medium and by-products. The neutralization is done after dispersing the precipitate in at least 2 L of ethanol (80%) containing approximately 1.5% of acetic acid. The final pH value is adjusted approximately to 6.5. To remove all solvents (methanol or ethanol and isopropanol) remaining in the starch derivative, the precipitate is washed several times (at least 2 times) in excess of ethanol 80% and finally in absolute ethanol before drying at 40° C. overnight to obtain powders. The obtained DS can vary between 0.4 and 0.7.

Example 10

10.1. Partially Hydrolysis of Starch Using Isoamylase Processing

In another embodiment of the present invention, partially hydrolyzed starch (PHS) can be obtained by isoamylase (EC 3.2.1.68) which is able to cleave the branching points (or alpha-1,6 linkages) of amylopectin and release short linear chain amylose. The PHS preparation by isoamylase can be conducted under similar conditions as described above for AG, except about of 2000 isoamylase units/g of starch have been used instead of AG.

10.2. Carboxymethylation of Partially Hydrolyzed Starch (PHS) Obtained by Isoamylase Processing The carboxymethylation of PHS obtained by isoamylase is carried out under similar conditions as described above for carboxymethylation of PHS obtained by AG processing.

Example 11

11.1. Partially Hydrolysis of Starch Using Alpha-Amylase

In another embodiment of the present invention, it is possible to use alpha-amylase (EC 3.2.1.1) in order to reduce granule size of starch, because this enzyme can hydrolyzes the alpha-(1,4) glucan linkages in polysaccharides of three or more alpha-(1,4) linked D-glucose units. This enzyme can use alone or in combination with other enzymes such as AG. The PHS by alpha-amylase is prepared under similar conditions as described above for AG, except about of 250 AA units/g of starch have been used instead of AG.

11.2. Carboxymethylation of Partially Hydrolyzed Starch (PHS) Obtained by Alpha-Amylase Processing The carboxymethylation of PHS obtained by alpha-amylase is carried out under similar conditions as described above for carboxymethylation of PHS obtained by AG processing. However, the DS is higher in comparing with others and varied between 0.6 and 1.2.

Example 12

Figure 11:
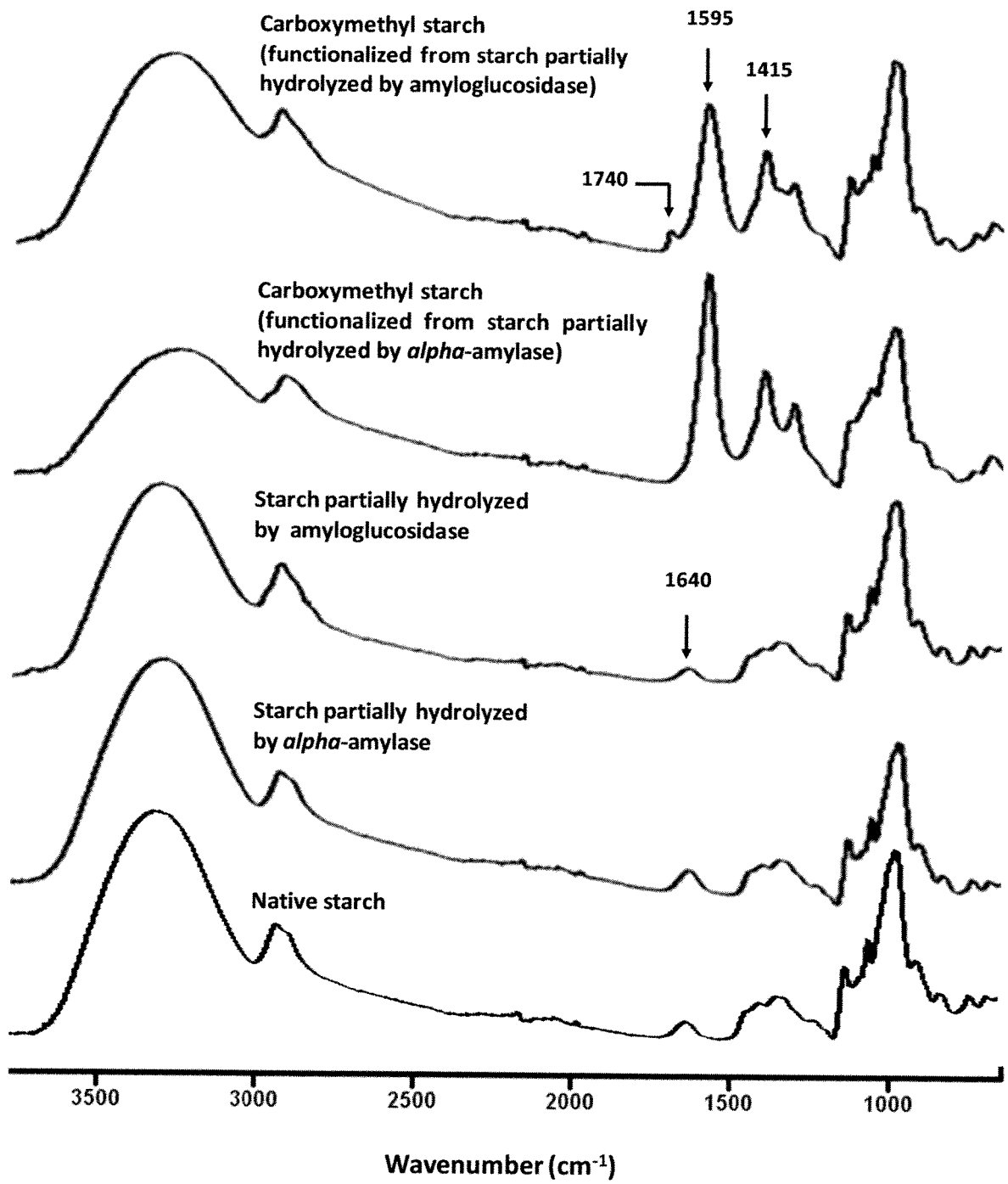
FIG. 11 illustrates FTIR spectra of native starch, of starch partially hydrolyzed by different enzymes and of carboxymethyl starch obtained from starch partially hydrolyzed by alpha-amylase or amyloglucosidase.

12. Characterization of Starch Partially Hydrolyzed by Different Enzymes 12.1. FTIR Analysis In general, no significant difference between native (not hydrolyzed) starch and PHS (FIG. 11) are observed by FTIR analysis. Similar observations for carboxymethyl starch functionalized from native starch and carboxymethyl starch functionalized with starches partially hydrolyzed by alpha-amylase or AG. As described previously, the absorption bands located at 1595 and 1415 $cm^{-1}$ are assigned to the asymmetric and symmetric stretching vibrations of carboxylate groups. It is of interest to mention that the intensity of these bands from carboxymethyl starch obtained from starch partially hydrolyzed by alpha-amylase are markedly high compared with that treated by AG. The explanation of this phenomenon is based probably on the size of starch granules. As mentioned previously, the treatment of starch by alpha-amylase can reduce the size of granules and consequently, an increase of the surface areas which are exposed to the contact with functionalizing agents yielding a higher DS.

12.2. X-Ray Diffraction Analysis

Figure 12:
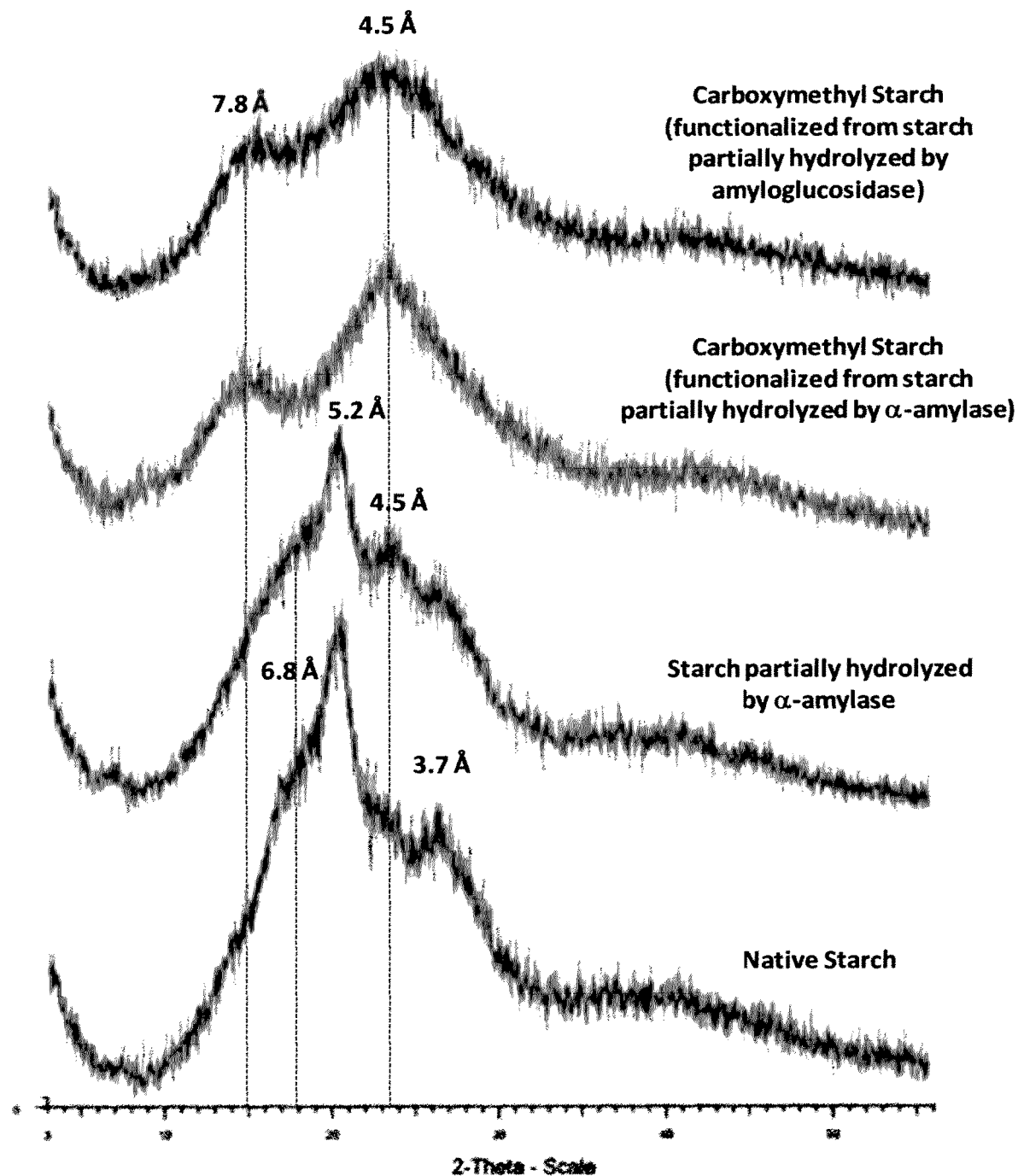
FIG. 12 illustrates X-Ray diffraction patterns of native starch, of starch partially hydrolyzed by different enzymes (alpha-amylase and amyloglucosidase) and of carboxymethyl starch obtained from starch partially hydrolyzed by alpha-amylase or by amyloglucosidase

X-ray diffraction patterns (FIG. 12) of native starch and of starch partially hydrolyzed by alpha-amylase present globally similar profile with except for the band at 4.5 Å (mainly contributing for single helix V-structure) whose intensity is significantly higher. For carboxymethyl starch obtained from starch partially hydrolyzed by alpha-amylase, the crystalline structure patterns are completely changed from double helix B-type for predominantly single helix V-type which is characterized by diffraction of 2 bands approximately at 4.5 Å and 7.8 Å.

Similar patterns for carboxymethylation of starch obtained from starch partially hydrolyzed by amyloglucosidase have been observed. However, its crystalline structure is less important and low ordered when compared to carboxymethyl starch obtained from starch partially hydrolyzed by alpha-amylase.

12.3. Scanning Electron Microscopy

The morphology and surface characteristics were examined at various magnifications (100-1000) with a Hitachi S-3400N Variable Pressure SEM (JEOL Ltd., Tokyo, JP) as described previously. The images are obtained with voltages approximately of 10 kV and high vacuum.

Figure 13:
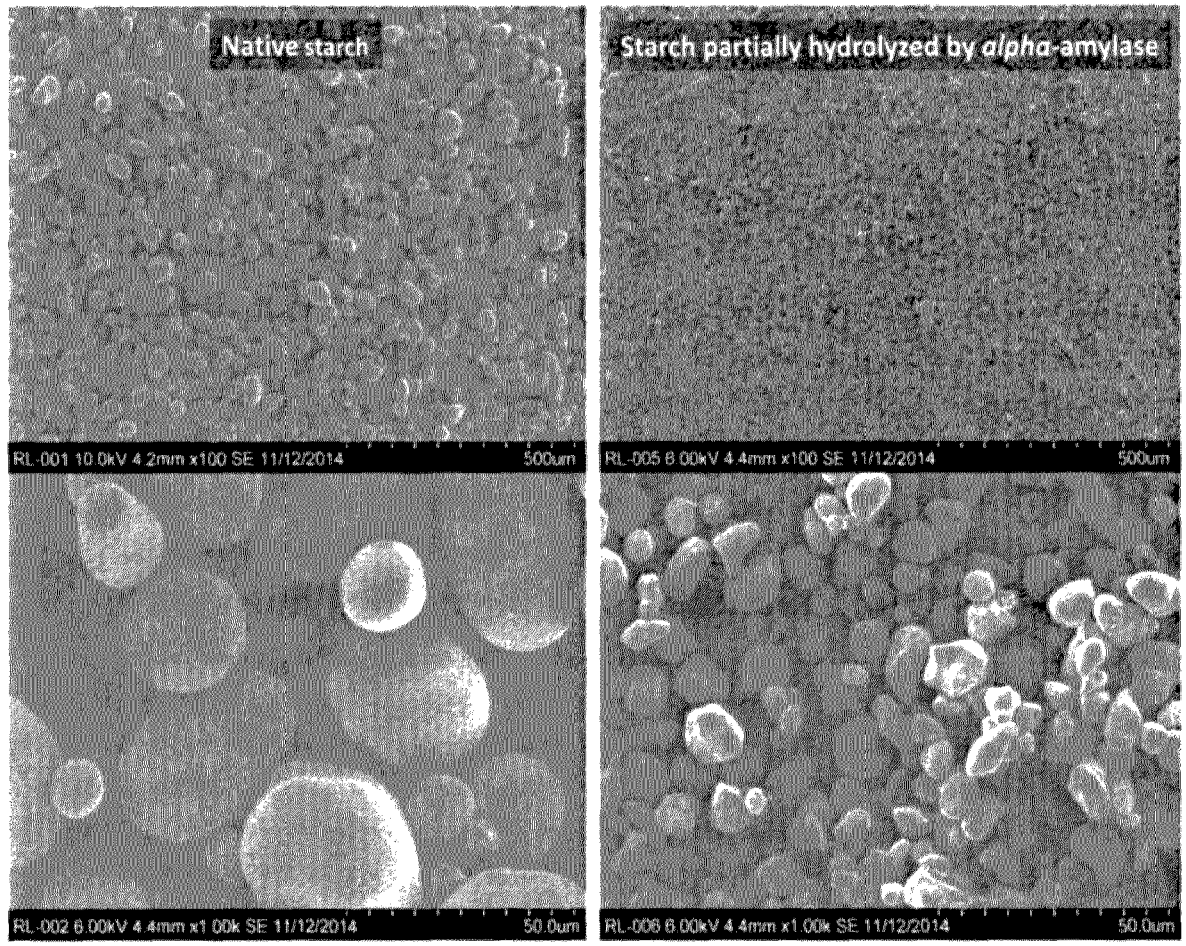
FIG. 13 illustrates Scanning Electron Microscopy of native starch and starch partially hydrolyzed by alpha-amylase.

The analysis of scanning electron microscopy (FIG. 13) showed that there are marked differences in terms of morphology and surface characteristics between native starch and starch partially hydrolyzed by alpha-amylase. Generally, the native starch granules are predominantly round or oval in shape, with smooth surface and size varied between 40-80 µm. In contrast, granules of starch partially hydrolyzed by alpha-amylase present an irregular form, oval forms and significantly smaller (approximately 4-8 times smaller than native starch with size between 4-10 µm). This observation is permitted to explain why starch treated by alpha-amylase possessing a higher DS compared with that treated by other enzymes. As mentioned previously, the smaller the granule size, the higher surface areas are exposed in contact with reagents and leading a higher yield of functionalized starch.

With regard for starch partially hydrolyzed by amyloglucosidase, significant changes in shape have been noticed when comparing with native starch, and the surface is irregular, similarly as for the starch treated by alpha-amylase and the granule size can vary between 25-50 µm.

Figure 14:
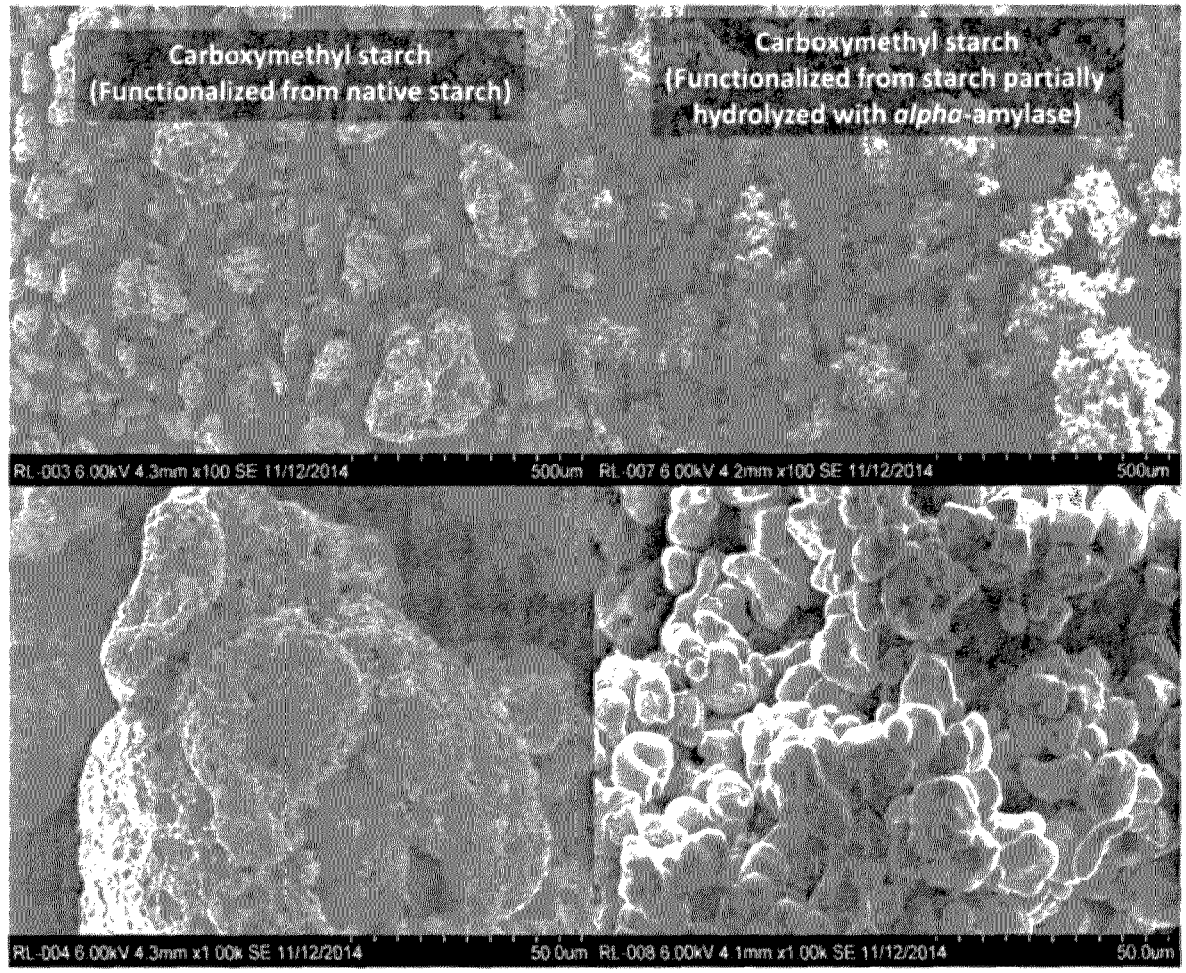
FIG. 14 illustrates Scanning Electron Microscopy of carboxymethyl starches obtained from functionalization of native starch and of starch partially hydrolyzed by alpha-amylase.

After carboxymethylation of native starch, its granules are considerably changed from the oval shape with smooth surface to the irregular shape with rough surface. In addition, certain granules are bonded together and formed aggregates (FIG. 14).

For carboxymethyl starch obtained from starch partially hydrolyzed by alpha-amylase, a smooth surface and a large variety in (irregular) shape including spherical, elongate or flat forms and, for certain, having an undulating surface are observed. It is of interest to mention that majority of granules are small and remained in grape (FIG. 14).

Figure 15:
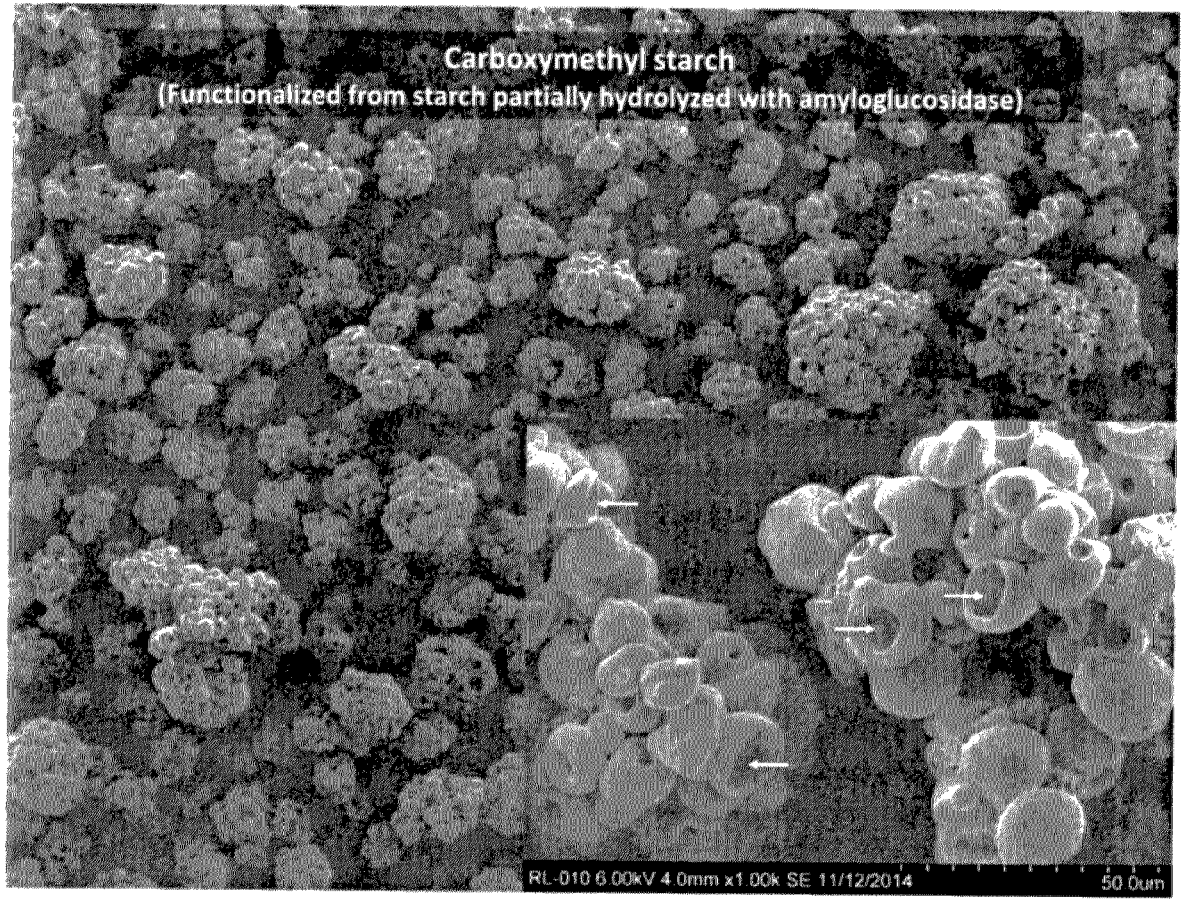
FIG. 15 illustrates Scanning Electron Microscopy of carboxymethyl starch obtained from functionalization of starch partially hydrolyzed by amyloglucosidase.
Figure 16:
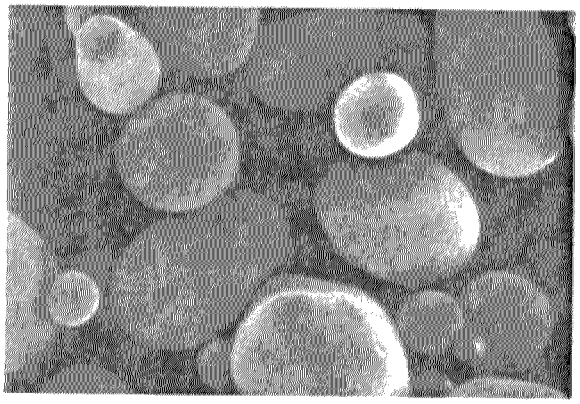
FIG. 16 illustrates Scanning Electron Microscopy granule morphology of native starch, of commercial carboxymethyl starch (starch glycolate) and of carboxymethyl starch in the present invention (obtained by carboxymethylation of starch partially hydrolyzed with amyloglucosidase).
Figure 16:
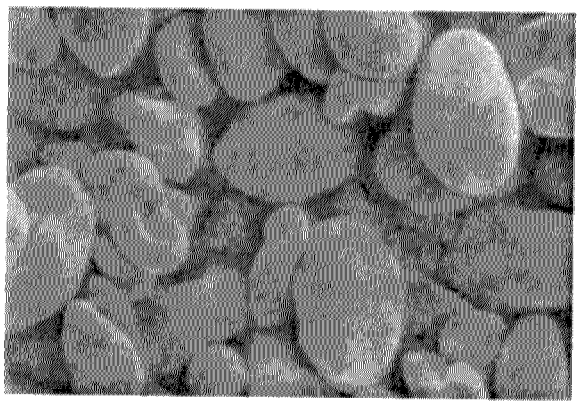
Figure 16:
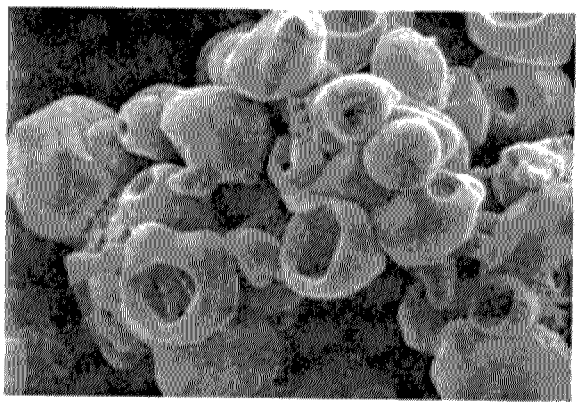

Concerning the carboxymethyl starch functionalized from starch partially hydrolyzed by amyloglucosidase (FIG. 15), the morphology of granules presents a unique and particular structure. Generally, these granules possess a slightly smooth surface and irregular shape which is characterized by the presence of a visible hole (or a centric hilum) with different diameter. For certain granules, these holes are large and appeared as small cups or bowls occurring in majority of granules with larger size. These granules are rather uniform approximately between 20-30 µm in size and adhered to each other forming grapes.

12.4. Comparison of the Granular Structure of Carboxymethyl Starch Obtained from Starch Partially Hydrolyzed by Aminoglucosidase with Commercial Carboxymethyl Starch In comparing granules between commercial carboxymethyl starch with native (no modified) starch, no significant difference in view of size and surface are noticed. For the shape, granules of commercial carboxymethyl starch are flat and ovoid or pear-shaped whereas those of native starch are rather spherical. In contrast, there are wide differences compared to native starch and commercial carboxymethyl starch and granules of carboxymethyl starch of the present invention obtained from starch partially hydrolyzed by amyloglucosidase. They are of smaller, irregular shapes with the presence of a hole occurring on the surface in the majority of granules.

12.5. Comparison of BA Inclusion Capacity of Native Starch, Functionalized Starch and Partially Hydrolyzed Starch To compare the BA loading capacity, native starch, carboxymethyl starches obtained from native starch and from starch partially hydrolyzed by amyloglucosidase are selected. For the bioactive agent, omega-3 is used in this study. Indeed, the incorporation of omega-3 in these starch-based matrices is prepared as described previously in EXAMPLE 3 above, with slight modification. Practically, different amounts (0.5-5.0 g) of omega-3 are added in starch-based matrices (5 g). Only uniform powders without visible oil or liquid traces overflowing when compressed under tablet forms are selected for scanning electron microscopy.

The obtained results showed that the ratio of starch-based matrix/omega-3 is respectively 12:1 (w/w) for native starch, 2:1 (w/w) for carboxymethyl starch obtained from native starch and 1:1 (w/w) for carboxymethyl starch obtained from starch partially hydrolyzed by amyloglucosidase. These results showed that the carboxymethyl starch prepared from starch partially hydrolyzed presents a higher BA loading capacity. The explanation could be based on the helical structure of starch. As mentioned previously, only the single helix V-structure presents a distinctive center channel (hydrophobic cavity) and able to entrap BA inside the helix. Generally, native starch is composed mainly of double helices and very few single helix V-structures. For this reason, a higher amount of native starch is required to complex with omega-3. When starch carboxymethylated according to the methods of the present invention, a higher omega-3 loading is observed. The explanation of higher capacity of carboxymethyl starch is due mainly to the functionalization of starch which permitted to convert from double helices to single helix V-type structures.

In the present invention, the highest omega-3 loading capacity is observed for carboxymethyl starch obtained from starch partially hydrolyzed by amyloglucosidase. In fact, it appears that partially hydrolyzed starch used as starting material permits to obtain a more effective functionalization reaction and consequently, a higher yield of conversion from double helices to single helix V-type. In this case, the more the single helix V-type structure is present in the partially hydrolyzed starch, the more the BA loading capacity is important. Additionally, it is believed that CMS obtained from starch partially hydrolyzed by amyloglucosidase possesses granules more porous which contribute to the increasing of BA loading capacity.

When exposed to daylight for 3 days, only carboxymethyl starch/omega-3 complex powders preserved their initial aspect whereas native starch/omega-3 complex powders changed color from white to yellow. This color change indicates that an oxidation phenomenon occurred, probably due to ineffective protection provided by native starch.

Figure 17:
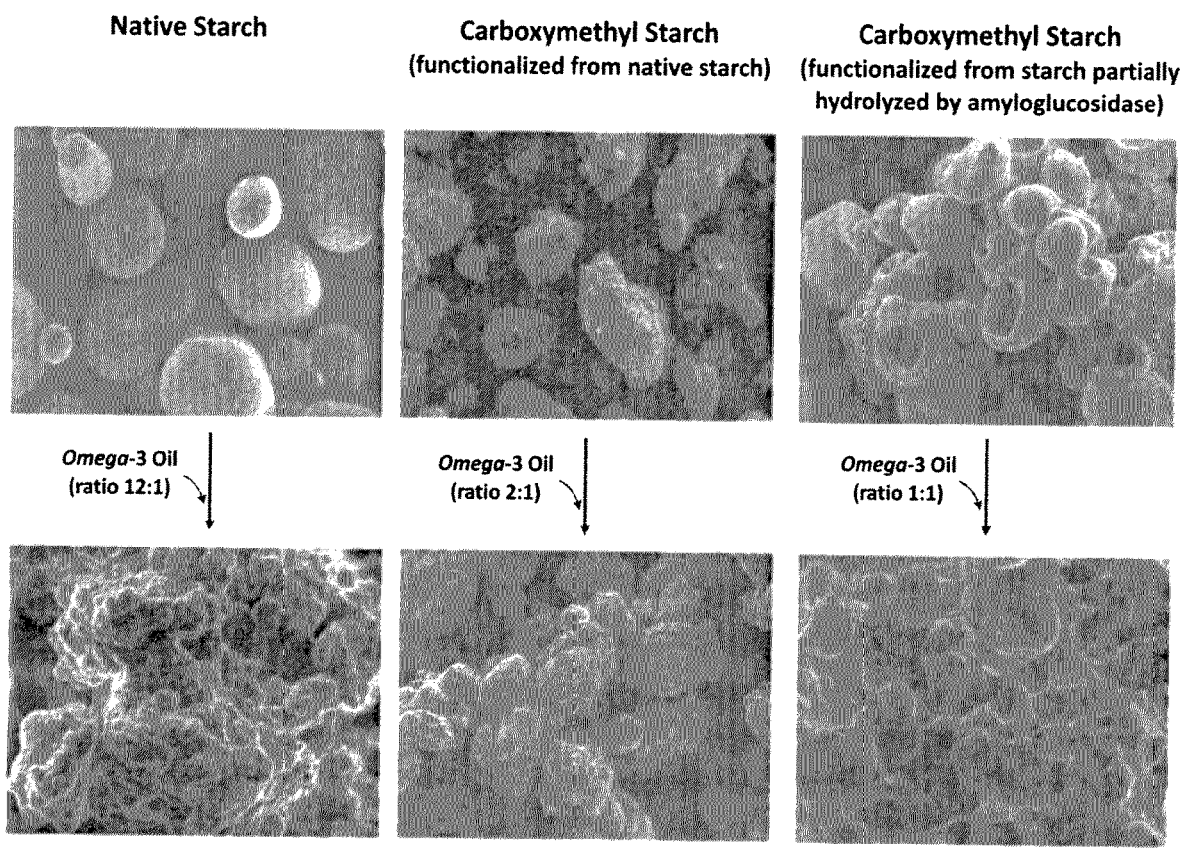
FIG. 17 illustrates different capacity to complex with omega-3 of native starch, carboxymethyl starch functionalized from native starch and carboxymethyl starch functionalized from starch partially hydrolyzed by amyloglucosidase.

Now referring in FIG. 17, the scanning electron microscopy showed that there is a significant change of starch granules after inclusion of omega-3. In fact, native starch/omega-3 (ratio 12:1, w/w) complex granules is changed from ovoid or pear-shaped with smooth surface to the compact agglomerated form with rough surface, probably due to the excess omega-3 remaining outside of starch granules. No visible change is observed for carboxymethyl starch (obtained from native starch)/omega-3 complex (ratio 2:1 w/w, synthesized by method of the present invention), except that granules are lightly adhered together.

With regard of complex formed of omega-3 and carboxymethyl starch obtained from starch hydrolyzed by amyloglucosidase, no distinctive granule shaped is observed. However, the contour of granules formed curved lines, wave-like shapes like the surface of the ocean. Generally, this complex presents a higher omega-3 loading capacity, probably due to its porous structure which can absorb a considerable amount of BA.

Example 13

Inclusion of Bioactive Agents in Carboxymethyl Starch Obtained from Starch Partially Hydrolyzed by Alpha-Amylase and Amyloglucosidase Different BA such as Astaxanthin, Cholecalciferol (Vit. D) and Artemisinin, etc. are incorporated in the matrices obtained from starch partially hydrolyzed by alpha-Amylase and Amyloglucosidase. The complexation is prepared similarly as described previously in EXAMPLE 6 and 7.

The obtained results showed that all carboxymethyl starches functionalized from starch partially hydrolyzed by enzymes present satisfactory mechanical properties with high BA loading capacity when compared with carboxymethyl starch obtained from native starch.

In comparing between carboxymethyl starch functionalized from starch partially hydrolyzed by alpha-amylase and that by amyloglucosidase, there is a slight difference. To obtain a high loading capacity and good mechanical properties (i.e. high solubility, rapid dispersibility and low viscosity, etc.) it is appropriate to use carboxymethyl starch obtained from starch partially hydrolyzed by alpha-amylase for BA with small size such as ibuprofen. Otherwise, it is better to use carboxymethyl starch obtained from starch partially hydrolyzed by amyloglucosidase for BA which possesses moderate or higher size such as Astaxanthin or Cholecalciferol. This is due to CMS obtained from starch partially hydrolyzed by amyloglucosidase which presents majoritarily a helix V-structure and of granules more porous.

Example 14

Succinylation of Starch

The preparation of succinyl starch is similar with that of carboxymethyl starch, as described previously in Example 9 with slight modifications.

Indeed, an amount of 80 g of starch is introduced in 1 L of solution of Ethanol (or methanol)/water (90/10, v/v) containing sodium hydroxide at least 3.0 M. Then, an amount of 150 g of succinic anhydride powders is directly added to the medium and the reaction is continued for at least 24 h (or more), at room temperature (22° C.) under mild stirring.

At the end of the reaction, the precipitate is separated by filtration (or by decantation) and washed thoroughly with an excess (~2 L) of ethanol 80% (or isopropanol) to eliminate a maximum of alkaline medium and by-products. The neutralization is done after dispersing the precipitate in at least 2 L of ethanol (80%) containing approximately 1.5% of lactic acid. The final pH value is adjusted approximately to 6.5. To remove all solvents (ethanol or isopropanol) remaining in the starch derivative, the precipitate is washed several times (at least 2 times) in excess of ethanol 80% and finally in absolute ethanol before drying at 40° C. overnight to obtain powders.

Example 15

Acetylation of Starch

The preparation of acetyl starch is carried out under similar conditions as used for the preparation of succinyl starch, except that acetic anhydride is used instead of succinic anhydride (125 g) and solvent for the reaction medium is isopropanol/water (90/10, v/v).

Example 16

Hydroxypropylation of Starch

The synthesis of hydroxypropyl starch is prepared under similar conditions as described for succinyl starch, except that the functionalizing reagent is propylene oxide (150 mL, density 0.83 g/cm$^3$) and solvent for the reaction medium is isopropanol/water (90/10, v/v).

Example 17

16.1. Determination of Degree of Substitution (DS)
16.1.1. Determination of DS of Succinyl Starch The DS is determined by direct titration method. A known mass of the sample (~100 mg) is dissolved in 100 mL of distilled water by stirring at 75° C. for 30 min. After cooling, the solution was titrated against 0.01 M standard NaOH solution and the DS was calculated by using the following equation:

$$DS = 162 \times (V_{NaOH} \times C_{NaOH})/m - 100(V_{NaOH} \times C_{NaOH})$$

where 162 is the molar mass (g/mol) of a glucose unit (GU), 100 is the net increase in the mass (g/mol) of an GU for each succinyl substituent, m is the mass of succinyl starch analyzed, $V_{NaOH}$ is the volume of standard NaOH solution consumed by titration, and $C_{NaOH}$ is the molarity of standard NaOH solution. The obtained DS vary between 0.36 and 0.51.

16.1.2. Determination of DS of Acetyl and Hydroxypropyl Starch

For acetyl and hydroxypropyl starch, the DS is determined by elemental analysis (instead of by titrimetry), because no charged groups are present in these functionalized starches. By elemental analysis, the DS of acetyl starch vary between 0.25 and 0.36 whereas the DS for hydroxypropyl starch is about of 0.42.

Example 18

FTIR Analysis of Starch Derivatives

Figure 18:
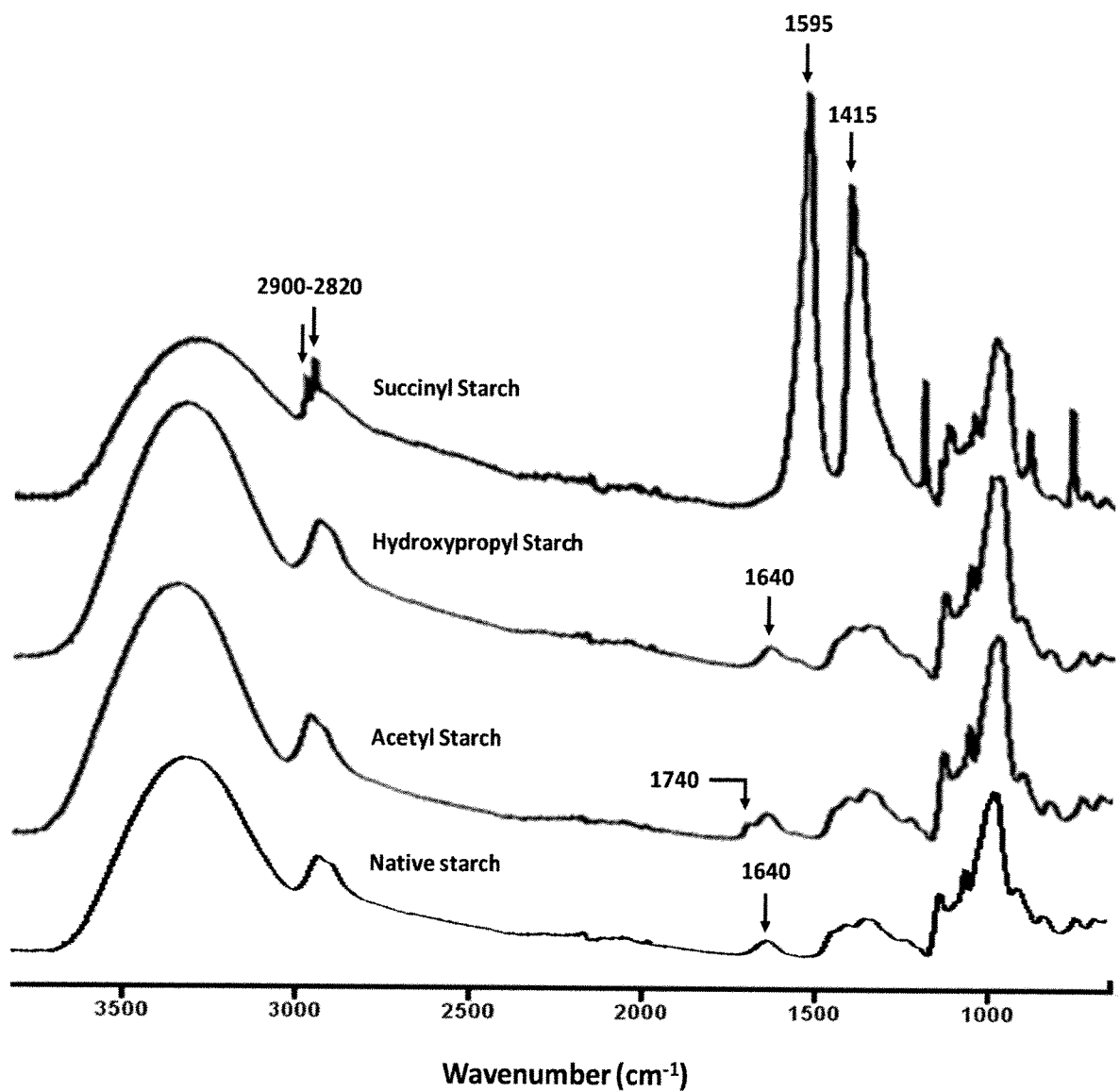
FIG. 18 illustrates FTIR spectra of native starch, of succinyl starch, acetyl starch and hydroxypropyl methyl starch.

Similar FTIR spectrum profile for succinyl starch (FIG. 18) when compared with carboxymethyl starch (FIG. 3) is observed, as described previously in the section 1.3.2. (Fourier Transform Infrared (FTIR) Analysis of EXAMPLE 1). The FTIR analysis allows to confirm that the reaction occurred by highlighting the presence of the carboxyl group (from succinyl residues) in the obtained powders. In fact, new absorption bands appear at 1595 and 1415 cm$^{-1}$ are assigned to carboxylate (asymmetric and symmetric stretching vibrations) anions after carboxymethylation of starch (FIG. 18). In addition, a moderate increasing in the spectral region of absorption bands located between 2925-2820 cm$^{-1}$ is observed. This phenomenon can be due to the presence of succinyl groups which are attributed to the stretching vibrations of alkyl chain (—CH$_2$—CH$_2$).

For acetyl starch, a new absorption band at 1740 cm$^{-1}$ is observed. This band is due to the stretching vibration of carbonyl (—C=O) from acetyl groups.

Referring to FTIR spectrum of hydroxypropyl starch, no significant difference is noticed when compared with that of native starch. However, a little increase of absorption bands in spectral region between 2925-2820 cm$^{-1}$ is observed. This observation is due to the overlapping stretching vibrations of (C—H) from alkyl chain (—CH$_2$— and —CH$_3$).

Example 19

Inclusion of Omega-3 in Different Starch Derivatives

In this study, omega-3 are used as BA in order to compare the loading capacity not only between succinyl, acetyl and hydroxypropyl starch, but also with carboxymethyl starch obtained as described in EXAMPLE 1. The incorporation of omega-3 in these starch derivatives is prepared as described previously in EXAMPLE 3. Practically, different amounts (0.5-5.0 g) of omega-3 are added in different starch-based matrices and only uniform powders without visible oil or liquid traces overflowing when compressed under tablet forms are selected.

The obtained results showed that the ratio of starch-based matrix/omega-3 is respectively 4:3 (w/w) for succinyl starch, 4:1 (w/w) for acetyl starch and 2:1 (w/w) for hydroxypropyl starch.

These results showed that the succinyl starch presents an omega-3 loading capacity higher than hydroxypropyl or acetyl starch, and even better than carboxymethyl starch (CMS/omega-3, 2:1 weight ratio). Lower BA loading capacity noticed for acetyl starch, was probably due to the acetate functional groups which are too small to alter or to disorganize completely the double helix structure to adopt a single structure. Furthermore, acetate groups are generally hydrophobic and are possibly directed inside the center cavity of helix, instead of remaining outside. This phenomenon can reduce or hinder the center cavity preventing thus the penetration or incorporation of omega-3. It is also important to mention that succinyl starch/omega-3 complex present a clear solution when dissolved in water or biological media. However, the solution is more viscous compared with other starch derivative/omega-3 complexes.

Example 20

Inclusion of Other Bioactive Agent in Different Starch Derivatives

Different BA such as Astaxanthin, Cholecalciferol (Vit. D) and Artemisinin, etc. have been incorporated incorporated in the matrices obtained from succinyl, acetyl and hydroxypropyl starch. The complexation was prepared similarly as described previously in EXAMPLE 6 and 7.

Similar behaviors for succinyl, acetyl and for hydroxypropyl starch complexing with omega-3 in terms of loading capacity and mechanical properties were noticed.

While preferred embodiments have been described above and illustrated in the accompanying drawings, it will be evident to those skilled in the art that modifications may be made without departing from this disclosure. Such modifications are considered as possible variants are comprised in the scope of the disclosure.

The invention claimed is:

1. A powder composition comprising:
   a carboxymethylated starch powder prepared by the following process:
     (a) placing a native starch and sodium monochloroacetate (SMCA) in an alkaline solvent-water medium having a solvent:water ratio of from about 70% to about 95% (vol/vol) solvent in water and at least 3 M sodium hydroxide (NaOH), and stirring for at least 10 hours at a temperature of from about 22° C. to about 28° C. to generate a carboxymethylated starch; and
     (b) washing and drying the carboxymethylated starch from step (a) to generate the carboxymethylated starch powder,
   and
   a poorly water-soluble or water insoluble bioactive agent, forming a water-soluble or water dispersible inclusion complex with said carboxymethylated starch powder,
   wherein said carboxymethylated starch powder and said bioactive agent are present in a ratio of about 4:1 to about 1:1 w/w.

2. The powder composition of claim 1, wherein said carboxymethylated starch has a degree of substitution (DS) from about 0.25 to about 1.5.

3. The powder composition of claim 1, wherein said carboxymethylated starch has a DS from about 0.4 to about 0.7.

4. The powder composition of claim 1, wherein said native starch is a corn starch, a potato starch, a pea starch, a rice starch, a bean starch, a wheat starch, or combinations thereof.

5. The powder composition of claim 4, wherein said native starch is a potato starch.

6. The powder composition of claim 1, wherein said solvent-water medium is an alcohol-water medium.

7. The powder composition of claim 6, wherein said alcohol-water medium is an ethanol-water medium or isopropanol-water medium.

8. The powder composition of claim 1, wherein said bioactive agent is a simple fatty acid, a lipid compound, a complex lipid, an antibiotic, a protein, a peptide, a pharmaceutically active ingredient or combinations thereof.

9. The powder composition of claim 8, wherein said simple fatty acid is alpha-linolenic acid, eicosapentaenoic acid, docosahexaenoic acid, or combinations thereof.

10. The powder composition of claim 8, wherein said complex lipid is a glyceride, a carotenoid, a terpenoid, an isoprenoid, a with anolide, a cholesterol, a phytosterol, a liposoluble vitamin, a stilbenoid, or combinations thereof.

11. The powder composition of claim 10, wherein said glyceride is omega-3 monoglyceride, omega-3 diglyceride, omega-3 triglycerides, or combinations thereof.

12. A pharmaceutical composition comprising:
   the powder composition of claim 1, and
   a pharmaceutically acceptable carrier.

13. The pharmaceutical composition of claim 12, wherein said bioactive agent is artemisinin or its derivatives.

14. A method of treating malaria comprising administering to a subject in need thereof the powder composition of claim 1, wherein said bioactive agent is artemisinin.

* * * * *